(12) United States Patent
Berka et al.

(10) Patent No.: US 6,221,644 B1
(45) Date of Patent: *Apr. 24, 2001

(54) POLYPEPTIDES HAVING PHYTASE ACTIVITY AND NUCLEIC ACIDS ENCODING SAME

(75) Inventors: Randy M. Berka; Michael W. Rey, both of Davis; Alan V. Klotz, Dixon, all of CA (US)

(73) Assignee: Novo Nordisk Biotech, Inc., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/163,642

(22) Filed: Sep. 30, 1998

Related U.S. Application Data

(63) Continuation of application No. 08/819,825, filed on Mar. 18, 1997, now Pat. No. 5,866,118, which is a continuation-in-part of application No. 08/617,235, filed on Mar. 18, 1996, now abandoned.

(51) Int. Cl.⁷ ............................... C12N 9/16; C12Q 1/68; A61K 38/46
(52) U.S. Cl. ............................... 435/196; 436/6; 424/94.6
(58) Field of Search ...................... 435/196, 6; 424/94.6

(56) References Cited

U.S. PATENT DOCUMENTS 5,866,118 * 2/1999 Berka et al. .................. 424/94.6

FOREIGN PATENT DOCUMENTS

| 0 420 358 A1 | 4/1991 | (EP) . |
| 0 684 313 A2 | 11/1995 | (EP) . |
| WO 96/28567 | 9/1996 | (WO) . |

OTHER PUBLICATIONS

Knuckles et al. (1987) Journal of Food Science 52(3) :719–721.

* cited by examiner

Primary Examiner—Ponnathapu Achutamurthy
Assistant Examiner—Peter P. Tung
(74) Attorney, Agent, or Firm—Elias Lambiris, Esq.; Robert L. Starnes

(57) ABSTRACT

The present invention relates to isolated polypeptides having phytase activity and isolated nucleic acid sequences encoding the polypeptides. The invention also relates to nucleic acid constructs, vectors, and host cells comprising the nucleic acid sequences as well as methods for producing the polypeptides. The present invention further relates to composite feeds and methods of reducing phytate levels.

14 Claims, 16 Drawing Sheets

AATTACGGAGTAGTGCCATTCGATGTTCATTGATCAACAGTCAACCGCAAGTTTCGTAGTATTTTCAAACTCCTCCACTGGCCGTGCG  90

TTGCGACACGACCTGCATGAGAATCGATGATCGATGATCTGATCATCTCGGGTTGAAGAGTCCACTTTATG  180

ACCAGGGGATTGATTTTCAATGCGTTGGTTGTTGTTCATCCGATTCATGAACAAGTGGACATTATTATTATGATTGCACGTGTCCTAAG  270

CTGCAAGTACTATTGAATAGTGCTTCAATGCTACCATGATCGGACACCAACACTCATGGAAGCCCGCCCCTAGCCGGACAGATCTGGCACA  360

CGCATCGTGCTGATATAAAAAGACTGCCAAATGCCGAAGACGAAATGCAGCCCGCAGAGTGATTGCCGTCATGGCGGGA  450
                                                                M  A  G

TAGGTTTGGGGTCCTTTCTGGTCTGCTGCAATT gtacgcattcttctagaccctaattatagaggtctgttgctgatat tctgact  540
I  G  L  G  S  F  L  V  L  L  Q  F agTTCGGCATTATTGACGGCCTCCGCCGGCCATTCCTGCGCCTCCTCTTCTGGAGGAAGCATCCCAACGTGGACATGCCGCCACTGGGGCCAG  630
   S  A  L  L  T  A  S  P  A  I  P  P  F  W  R  K  K  H  P  N  V  D  I  A  R  H  W  G  Q TACTCGCCCTTCTCTCGCTGCCGGAGTCTCTGAAATCTCGCCTGCCGTGCCCAAGGGGTGTCGAGTTTGTGCAGGTGCTGTCC  720
Y  S  P  F  F  S  L  A  E  V  S  E  I  S  P  A  V  P  K  G  C  R  V  E  F  V  Q  V  L  S CGGCACGGAGCTCGTATCCTACTGCTCACAAGAGTGAAGTCTACGCCGAGTTGCTTCAAAGGATCCAGGACACTGCGACCGAGTTCAAG  810
R  H  G  A  R  Y  P  T  A  H  K  S  E  V  Y  A  E  L  L  Q  R  I  Q  D  T  A  T  E  F  K

FIG. 2A

```
GGCGATTTGCCTTTCTCCGAGACTATGCCTATCATCTCGGTGCCGATAATTTGACGCGGCTTTGGCGAGGACGAGATGATGAATCGGGC  900
 G  D  F  A  F  L  R  D  Y  A  Y  H  L  G  A  D  N  L  T  R  F  G  E  E  Q  M  M  E  S  G

CGCCAGTTCTACCACCGGTATCGTGAGCAGGCCCGAGAGATTGTGCCATTTGTGCGTGCGCAGGCTCCGGCGAGTCATTGCCGTCGGCA  990
 R  Q  F  Y  H  R  Y  R  E  Q  A  R  E  I  V  P  F  V  R  A  A  G  S  A  R  V  I  A  S  A

GAGTTCTTCAACCGCGGATTCCAGGATGCCAAAGACCGGGATCCCAGTCGAACAAGGACCAGAGCCTGTGATCAACGTGATCATT   1080
 E  F  F  N  R  G  F  Q  D  A  K  D  R  D  P  R  S  N  K  D  Q  A  E  P  V  I  N  V  I  I

TCCGAAGAAACTGGCAGTAACAATACTCTGGATGGGCTGACGTGCCCGGCCGCAGAGGAGGCACCGGACCCAACCCAGCCCGAGAGTTC  1170
 S  E  E  T  G  S  N  N  T  L  D  G  L  T  C  P  A  A  E  E  A  P  D  P  T  Q  P  A  E  F  F

CTGCAAGTTTTCGGCCCGCGTGTCTTGAAAAAGATCACTAAAACACATGCCGGGTGTGAACCTCACCTTGAGGATGTCCCGTTGTTCATG  1260
 L  Q  V  F  G  P  R  V  L  K  K  I  T  K  H  M  P  G  V  N  L  T  L  E  D  V  P  L  F  M

GATCTTTGTCCGTTTGACACGGTGGGCTCCGACCCAGTTCTTTTCCCACGGCAGCTCTCTCCGTTTGTCACTTGTTCACGGCCGACGAT  1350
 D  L  C  P  F  D  T  V  G  S  D  P  V  L  F  P  R  Q  L  S  P  F  C  H  L  F  T  A  D  D

TGGATGGCCTACGATTACTACTACACCCTCGACAAATACTACAGCCACGGCGGCGGCAGCGCATTTGGCCCGTCCCGCGGCGTCGGGGTTC  1440
 W  M  A  Y  D  Y  Y  Y  T  L  D  K  Y  Y  S  H  G  G  G  S  A  F  G  P  S  R  G  V  G  F
```

FIG. 2B

```
TTCCCGTTGGACGCTGTCCTCTACGCAGACTTTTCGCACGACAACACCATGACGGGCATCTTTTCCGCAATGGGCCTGTACAACGGCACA  1620
 F  P  L  D  A  V  L  Y  A  D  F  S  H  D  N  T  M  T  G  I  F  S  A  M  G  L  Y  N  G  T

AAGCCGCTGTCGACTGTCCAAGATTCAGCCTCCGACGGTGCAGCAGCGGATGGATATGCGGCATCGTGGACGGTGCCGTTCGCAGCGAGG  1710
 K  P  L  S  T  S  K  I  Q  P  P  T  G  A  A  A  D  G  Y  A  A  S  W  T  V  P  F  A  A  R

GCGTATGTGGAGTTGCTGCGATGTGAGACGGAAACGAGCTCTGAGGAGGAGGAGGGGGAGGACGAGCCGTTCGTGCGGGTTCTGGTG  1800
 A  Y  V  E  L  L  R  C  E  T  E  T  S  S  E  E  E  E  G  E  D  E  P  F  V  R  V  L  V

AATGATCGGGTTGTGCCGCTGCATGGTTGTCGGGTTGATCGATGGGGGAGGTGTCGGAGGATGAGTTGATTAAGGACTCACGTTTGCT  1890
 N  D  R  V  V  P  L  H  G  C  R  V  D  R  W  G  R  C  R  R  D  E  W  I  K  G  L  T  F  A

CGACAGGGTGGGCATTGGGATGCTGCTTTTGATTAGATGCTCATAGACATAACCCCATGATTCCGAATTGATGTTTTTAGATACAATCA  1980
 R  Q  G  G  H  W  D  R  C  F

CTGCGGAAAGGGAAATGATCCAAAAAGCGCCAGTCTAGTATAACTTTGCGAATCCGTTGACTTGTTCAGTCCTTGGTGTCGCCATCAACC  2070

AGGCCTGCCACAAGGTCCAATGTTCCGCTCTACATGGAGTCCGTCGCCGAGATCATTCCAGCGCCCAGCGCCACGGAGCTGTTCCGTTG  2160

AGGGTATCTGCCGTTGACCCCCGTGCTCACAGTCACA  2200
```

FIG.2C

```
  1  M A G I G L G S F L V L L L Q F S A L L T A S P A I P P F W R K K H P N V V D I  Thermomyces.phy
  1  M G V S A V L L P L Y L L L S G V T S G L A V P A S R N Q S S C D T V D Q G Y Q C  Aniger.phy 41  A R H W G Q Y S P F F S L A E V S E I S P A V P K G C R V E F V Q V L S R H G A  Thermomyces.phy
 41  F S E T S H L W G Q Y A P F F S L A N E S V I S P E V P A G C R V T F A Q V L S  Aniger.phy 81  R Y P T A H K S E V Y A E L L Q R I Q D T A T E F K G D F A F L R D Y A Y H L G  Thermomyces.phy
 81  R H G A R Y P T D S K G K K Y S A L I E E I Q Q N A T T F D G K Y A F L K T Y N  Aniger.phy 121  A D N L T R F G E E Q M M E S G R Q F Y H R Y R E Q A R E I V P F V R A A G S A  Thermomyces.phy
121  Y S L G A D D L T P F G E Q E L V N S G I K F Y Q R Y E S L T R N I V P F I R S  Aniger.phy 161  R V I A S A E F F N R G F Q D A K D R D P R S N K D Q A E P V I N V I I S E E T  Thermomyces.phy
161  S G S S R V I A S G K K F I E G F Q S T K L K D P R A Q P G Q S S P K I D V V I  Aniger.phy 201  G S N N T L D G L T C P A A E E A P D P T Q P A E F L Q V F G P R V L K K I T K  Thermomyces.phy
201  S E A S S S N N T L D P G T C T V F E D S E L A D T V E A N F T A T F V P S I R  Aniger.phy
```

FIG. 3A

```
241  H M P G V N L T L E D V P L F M D L C P F D T V G S D P V L F P R Q L S P F C H   Thermomyces.phy
241  Q R L E N D L S G V T L T D T E V T Y L M D M C S F D T I S T S T V D T K L S P   Aniger.phy 281  L F T A D D W M A Y D Y Y Y I L D K Y Y S H G G G S A F G P S R G V G F V N E L   Thermomyces.phy
281  F C D L F T H D E W I N Y D Y L Q S L K K Y Y G H G A G N P L G P T Q G V G Y A   Aniger.phy 321  I A R M I G N L P V K D H T T V N H T L D D N P E T F P L D A V L Y A D F S H D   Thermomyces.phy
321  N E L I A R L T H S P V H D D T S S N H T L D S S P A T F P L N S T L Y A D F S   Aniger.phy 361  N T M T G I F S A M G L Y N G T K P L S T S K I Q P P T G A A A D G Y A A S W T   Thermomyces.phy
361  H D N G I I S I L F A L G L Y N G T K P L S T T T V E N I T Q T D G F S S A W T   Aniger.phy 401  V P F A A R A Y V E L L R C E T E T S S E E E E G E D E P F V R L V N D R V   Thermomyces.phy
401  V P F A S R L Y V E M M Q C Q A E Q E P L V R V L V N D R V V P L H G C P V D A   Aniger.phy 441  V P L H G C R V D R W G R C R R D E W I K G L T F A R Q G G H W D R C F   Thermomyces.phy
441  L G R C T R D S F V R G L S F A R S G G D W A E C F A   Aniger.phy
```

FIG. 3B

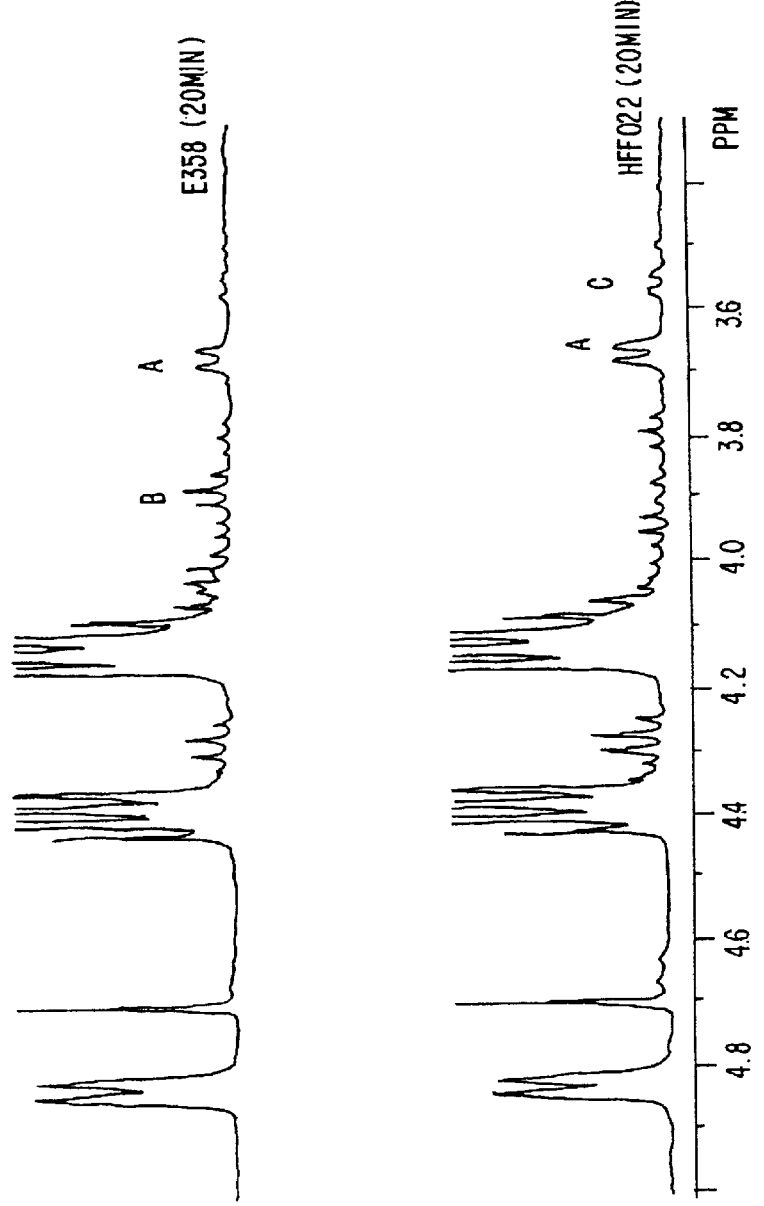

US 6,221,644 B1

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2200 base pairs
      (B) TYPE: nucleic acid
      (C) STRANDEDNESS: single
      (D) TOPOLOGY: linear (xi) SEQUENCE DESCRIPTION: SEQ ID NO:1:

```
AATTACGGAG TAGTTGCCAT TCGATGTTCA TTGATCAACA GTCAACCGCA AGTTTCGTAG      60

TATTTTCCAA ACTCCTCCAC TGGCCGTGCG TTGCGACACG ACCTGCATGA GAATCGATCG     120

ATCGATCGAT GATCGCTCAG GATGATCTGA TCATCTCGGG TTGGAAGAGT CCACTTTATG     180

ACCAGGGGAT TGATTTTTCA ATGCGTTGGT TGTTGTTCAT CCGATTCATG AACAAGTGGA     240

CATTATTATT ATGATTGCAC GTGTCCTAAG CTGCAAGTAC TATTGAATAG TGCTTCAATG     300

CTACCATGAT CGGACACCAA CACTCATGGA AGCCCGCCCC TAGCCGGCAG ATCTGGCACA     360

CGCATCGTGC TGATATAAAA AGACTGCCAA ATGCCGAAGA CGAAATGCAG CAACGTTCAG     420

CCCGCAGAGT GATTGCCGTC ATGGCGGGGA TAGGTTTGGG GTCCTTTCTG GTCCTGCTGC     480

TGCAATTGTA CGCATTCTTC TAGACCCTAA TTATAGAGGT CTGTTGCTGA TATTCTGACT     540

AGTTCGGCAT TATTGACGGC CTCGCCGGCC ATTCCTCCTT TCTGGAGGAA GAAGCATCCC     600

AACGTGGACA TTGCCCGCCA CTGGGGCCAG TACTCGCCCT TCTTCTCGCT GGCCGAGGTC     660
```

```
TCTGAAATCT CGCCTGCGGT GCCCAAGGGC TGTCGTGTCG AGTTTGTGCA GGTGCTGTCC      720

CGGCACGGAG CTCGGTATCC TACTGCTCAC AAGAGTGAAG TCTACGCCGA GTTGCTTCAA      780

AGGATCCAGG ACACTGCGAC CGAGTTCAAG GGCGATTTTG CCTTTCTCCG AGACTATGCC      840

TATCATCTCG GTGCCGATAA TTTGACGCGC TTTGGCGAGG AGCAGATGAT GGAATCGGGC      900

CGCCAGTTCT ACCACCGGTA TCGTGAGCAG GCCCGAGAGA TTGTGCCATT TGTGCGTGCG      960

GCAGGCTCCG CGCGAGTCAT TGCGTCGGCA GAGTTCTTCA ACCGCGGATT CCAGGATGCC     1020

AAAGACCGGG ATCCCAGGTC GAACAAGGAC CAGGCAGAGC CTGTGATCAA CGTGATCATT     1080

TCCGAAGAAA CTGGCAGTAA CAATACTCTG GATGGGCTGA CGTGCCCGGC GGCCGAGGAG     1140

GCACCGGACC CAACCCAGCC CGCAGAGTTC CTGCAAGTTT TCGGCCCGCG TGTCTTGAAA     1200

AAGATCACTA AACACATGCC GGGTGTGAAC CTCACCTTGG AGGATGTCCC GTTGTTCATG     1260

GATCTTTGTC CGTTTGACAC GGTGGGCTCC GACCCAGTTC TTTTCCCACG GCAGCTCTCT     1320

CCGTTTTGTC ACTTGTTCAC GGCCGACGAT TGGATGGCCT ACGATTACTA CTACACCCTC     1380

GACAAATACT ACAGCCACGG CGGCGGCAGC GCATTTGGCC CGTCCCGCGG CGTCGGGTTC     1440

GTCAACGAGC TGATTGCGCG TATGACGGGA AATCTTCCCG TCAAGGACCA CACAACAGTC     1500

AACCACACTC TCGATGACAA CCCGGAAACT TTCCCGTTGG ACGCTGTCCT CTACGCAGAC     1560

TTTTCGCACG ACAACACCAT GACGGGCATC TTTTCCGCAA TGGGCCTGTA CAACGGCACA     1620

AAGCCGCTGT CGACGTCCAA GATTCAGCCT CCGACGGGTG CAGCAGCGGA TGGATATGCG     1680

GCATCGTGGA CGGTGCCGTT CGCAGCGAGG GCGTATGTGG AGTTGCTGCG ATGTGAGACG     1740

GAAACGAGCT CTGAGGAGGA GGAGGAGGGG GAGGACGAGC CGTTCGTGCG GGTTCTGGTG     1800

AATGATCGGG TTGTGCCGCT GCATGGTTGT CGGGTTGATC GATGGGGAG GTGTCGGAGG     1860

GATGAGTGGA TTAAGGGACT CACGTTTGCT CGACAGGGTG GGCATTGGGA TCGCTGCTTT     1920

TGATTAGATG CTCATAGACA TAACCCCATG ATTCCGAATT GATGTTTTTA GATACAATCA     1980

CTGCGGAAAG GGAAATGATC CAAAAAGCGC CAGTCTAGTA TAACTTTGCG AATCCGTTGA     2040

CTTGTTCAGT CCTTGGTGTC GCCATCAACC AGGCCTGCCA CAAGGTCCAA TGTTCCCGCT     2100

CTACATGGAG TCCGTCGTCG CCGAGATCAT CCACGCCCAG CGCACGGAGC TGTTCCGTTG     2160

AGGGTATCTG CCGTGGTTGA CCCCCGTGCT CACAGTCACA                           2200
```

(2) INFORMATION FOR SEQ ID NO:2:

(i) SEQUENCE CHARACTERISTICS:
        (A) LENGTH: 475 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Ala Gly Ile Gly Leu Gly Ser Phe Leu Val Leu Leu Gln Phe
 1               5                  10                  15

Ser Ala Leu Leu Thr Ala Ser Pro Ala Ile Pro Pro Phe Trp Arg Lys
            20                  25                  30

Lys His Pro Asn Val Asp Ile Ala Arg His Trp Gly Gln Tyr Ser Pro
        35                  40                  45

Phe Phe Ser Leu Ala Glu Val Ser Glu Ile Ser Pro Ala Val Pro Lys
    50                  55                  60
```

-continued

```
Gly Cys Arg Val Glu Phe Val Gln Val Leu Ser Arg His Gly Ala Arg
 65                  70                  75                  80

Tyr Pro Thr Ala His Lys Ser Glu Val Tyr Ala Glu Leu Leu Gln Arg
                 85                  90                  95

Ile Gln Asp Thr Ala Thr Glu Phe Lys Gly Asp Phe Ala Phe Leu Arg
                100                 105                 110

Asp Tyr Ala Tyr His Leu Gly Ala Asp Asn Leu Thr Arg Phe Gly Glu
            115                 120                 125

Glu Gln Met Met Glu Ser Gly Arg Gln Phe Tyr His Arg Tyr Arg Glu
    130                 135                 140

Gln Ala Arg Glu Ile Val Pro Phe Val Arg Ala Ala Gly Ser Ala Arg
145                 150                 155                 160

Val Ile Ala Ser Ala Glu Phe Phe Asn Arg Gly Phe Gln Asp Ala Lys
                165                 170                 175

Asp Arg Asp Pro Arg Ser Asn Lys Asp Gln Ala Glu Pro Val Ile Asn
                180                 185                 190

Val Ile Ile Ser Glu Glu Thr Gly Ser Asn Asn Thr Leu Asp Gly Leu
            195                 200                 205

Thr Cys Pro Ala Ala Glu Glu Ala Pro Asp Pro Thr Gln Pro Ala Glu
    210                 215                 220

Phe Leu Gln Val Phe Gly Pro Arg Val Leu Lys Lys Ile Thr Lys His
225                 230                 235                 240

Met Pro Gly Val Asn Leu Thr Leu Glu Asp Val Pro Leu Phe Met Asp
                245                 250                 255

Leu Cys Pro Phe Asp Thr Val Gly Ser Asp Pro Val Leu Phe Pro Arg
                260                 265                 270

Gln Leu Ser Pro Phe Cys His Leu Phe Thr Ala Asp Asp Trp Met Ala
            275                 280                 285

Tyr Asp Tyr Tyr Tyr Thr Leu Asp Lys Tyr Tyr Ser His Gly Gly Gly
    290                 295                 300

Ser Ala Phe Gly Pro Ser Arg Gly Val Gly Phe Val Asn Glu Leu Ile
305                 310                 315                 320

Ala Arg Met Thr Gly Asn Leu Pro Val Lys Asp His Thr Thr Val Asn
                325                 330                 335

His Thr Leu Asp Asp Asn Pro Glu Thr Phe Pro Leu Asp Ala Val Leu
            340                 345                 350

Tyr Ala Asp Phe Ser His Asp Asn Thr Met Thr Gly Ile Phe Ser Ala
    355                 360                 365

Met Gly Leu Tyr Asn Gly Thr Lys Pro Leu Ser Thr Ser Lys Ile Gln
370                 375                 380

Pro Pro Thr Gly Ala Ala Ala Asp Gly Tyr Ala Ala Ser Trp Thr Val
385                 390                 395                 400

Pro Phe Ala Ala Arg Ala Tyr Val Glu Leu Leu Arg Cys Glu Thr Glu
                405                 410                 415

Thr Ser Ser Glu Glu Glu Glu Glu Gly Glu Asp Glu Pro Phe Val Arg
            420                 425                 430

Val Leu Val Asn Asp Arg Val Val Pro Leu His Gly Cys Arg Val Asp
    435                 440                 445

Arg Trp Gly Arg Cys Arg Arg Asp Glu Trp Ile Lys Gly Leu Thr Phe
    450                 455                 460

Ala Arg Gln Gly Gly His Trp Asp Arg Cys Phe
465                 470                 475
```

(2) INFORMATION FOR SEQ ID NO:3:

(i) SEQUENCE CHARACTERISTICS:
        (A) LENGTH: 467 amino acids
        (B) TYPE: amino acid
        (C) STRANDEDNESS: single
        (D) TOPOLOGY: linear (xi) SEQUENCE DESCRIPTION: SEQ ID NO:3:

```
Met Gly Val Ser Ala Val Leu Leu Pro Leu Tyr Leu Ser Gly Val
 1               5                  10                  15

Thr Ser Gly Leu Ala Val Pro Ala Ser Arg Asn Gln Ser Ser Cys Asp
            20                  25                  30

Thr Val Asp Gln Gly Tyr Gln Cys Phe Ser Glu Thr Ser His Leu Trp
        35                  40                  45

Gly Gln Tyr Ala Pro Phe Phe Ser Leu Ala Asn Glu Ser Val Ile Ser
    50                  55                  60

Pro Glu Val Pro Ala Gly Cys Arg Val Thr Phe Ala Gln Val Leu Ser
65                  70                  75                  80

Arg His Gly Ala Arg Tyr Pro Thr Asp Ser Lys Gly Lys Lys Tyr Ser
                85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320

Asn Glu Leu Ile Ala Arg Leu Thr His Ser Pro Val His Asp Asp Thr
                325                 330                 335

Ser Ser Asn His Thr Leu Asp Ser Ser Pro Ala Thr Phe Pro Leu Asn
            340                 345                 350

Ser Thr Leu Tyr Ala Asp Phe Ser His Asp Asn Gly Ile Ile Ser Ile
        355                 360                 365
```

```
Leu Phe Ala Leu Gly Leu Tyr Asn Gly Thr Lys Pro Leu Ser Thr Thr
    370                 375                 380

Thr Val Glu Asn Ile Thr Gln Thr Asp Gly Phe Ser Ser Ala Trp Thr
385                 390                 395                 400

Val Pro Phe Ala Ser Arg Leu Tyr Val Glu Met Met Gln Cys Gln Ala
                405                 410                 415

Glu Gln Glu Pro Leu Val Arg Val Leu Val Asn Asp Arg Val Val Pro
                420                 425                 430

Leu His Gly Cys Pro Val Asp Ala Leu Gly Arg Cys Thr Arg Asp Ser
        435                 440                 445

Phe Val Arg Gly Leu Ser Phe Ala Arg Ser Gly Gly Asp Trp Ala Glu
    450                 455                 460

Cys Phe Ala
465

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:4:

ATTTAAATGG CGGGGATAGG TTTGG                                    25

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CTTAATTAAT CAAAAGCAGC GATCCC                                   26
```

POLYPEPTIDES HAVING PHYTASE ACTIVITY AND NUCLEIC ACIDS ENCODING SAME

CROSS-REFERENCE TO OTHER APPLICATIONS

This application is a continuation of U.S. application Ser. No. 08/819,825, now U.S. Pat. No. 5,866,118, filed Mar. 18, 1997, which is a continuation-in-part of U.S. application Ser. No. 08/617,235 filed Mar. 18, 1996, now abandoned, the contents of which are fully incorporated herein by reference.

BACKGROUND OF THE INVENTION

1. Field of the Invention

The present invention relates to isolated polypeptides having phytase activity and isolated nucleic acid sequences encoding the polypeptides. The invention also relates to nucleic acid constructs, vectors, and host cells comprising the nucleic acid sequences as well as methods for producing the polypeptides. The invention further relates to compositions comprising the polypeptides and methods of use thereof.

2. Description of the Related Art

Phytases (myo-inositol hexakisphosphate phosphohydrolases, EC 3.1.3.8) catalyze the hydrolysis of phytate (myo-inositol hexakisphosphate) to (1) myo-inositol, (2) mono-, di-, tri-, tetra- and penta-phosphates thereof and (3) inorganic phosphate. In the following, for short, the above compounds are sometimes referred to as IP6, I, IP1, IP2, IP3, IP4, IP5 and P, respectively. This means that by action of a phytase, IP6 is degraded into inorganic phosphate and one or more of the components IP5, IP4, IP3, IP2, IP11 and I. Alternatively, myo-inositol carrying in total n phosphate groups attached to positions p, q, r, . . . is denoted $(Ins(p,q,r,\ldots)P_n)$.

Two different types of phytases are known: A so-called 3-phytase (myo-inositol hexakisphosphate 3-phosphohydrolase, EC 3.1.3.8) and a so-called 6-phytase (myo-inositol hexakisphosphate 6-phosphohydrolase, EC 3.1.3.26). The 3-phytase hydrolyzes first the ester bond at the 3-position, whereas the 6-phytase hydrolyzes first the ester bond at the 6-position. The remaining ester bonds of the resulting IP5 substrate (whether the 1,2,4,5,6 -IP5 or the 1,2,3,4,5-IP5) are subsequently hydrolyzed at different rates. Also the rate of hydrolysis of the components IP4, IP3, IP2 and IP1 seems to be variable, if hydrolyzed at all.

Phytase-producing microorganisms include bacteria such as *Bacillus subtilis* (Paver and Jagannathan, 1982, *Journal of Bacteriology* 151: 1102–1108) and Pseudomonas (Cosgrove, 1970, Australian Journal of Biological Sciences 23: 1207–1220); yeast such as *Saccharomyces cerevisiae* (Navini and Marcakis, 1984, *Lebensmittei Wissenschaft und Technologie* 17: 24–26; and fungi of the Aspergillus genus such as *Aspergillus terreus* (Yamada et al., 1986, *Agricultural Biological Chemistry* 322: 1275–1282).

The cloning and expression of the phytase genes from *Aspergillus niger* var. *awamori* by Piddington et al. (1993, *Gene* 133: 55–62) and *Aspergillus niger* (ficuum) by van Hartingsveldt et al. (1993, *Gene* 127: 87–94; EP 420 358) have been disclosed.

Phytic acid is the primary storage form of phosphate in cereal grains, legumes, and oilseeds, such as soy, which are the principal components of animal feeds. However, the presence of phytic acid in animal feeds for monogastric animals is undesirable because the phosphate moieties of phytic acid chelate essential minerals and possibly proteins making them nutritionally unavailable. Furthermore, phytate phosphorus passes through the gastrointestinal tract of monogastric animals and is not metabolized. Since phosphorus is an essential element for the growth of all organisms, livestock feed must be supplemented with inorganic phosphate. Thus, the art has described the use of phytases in feeds of monogastric animals.

Furthermore, since phytic acid is not metabolized by monogastric animals, it is excreted in manure. The amount of manure produced worldwide has increased significantly resulting from increased livestock production. The disposal of manure has caused an environmental problem in various locations around the world due to the accumulation of phosphate particularly in water. Thus, the art has also described the use of phytases for reducing the amount of phytate in manure.

There is a need in the art for new phytases with improved properties which can be produced in commercially significant quantities.

It is an object of the present invention to provide a new class of phytases, i.e., 3,6-phytases, i.e., phytases which attack both bonds of a phosphoester.

SUMMARY OF THE INVENTION

The present invention relates to isolated polypeptides having phytase activity selected from the group consisting of:

(a) a polypeptide having 3,6-phytase activity;
(b) a polypeptide with an amino acid sequence which has at least 60% identity with the amino acid sequence set forth in SEQ ID NO:2;
(c) a polypeptide which is encoded by a nucleic acid sequence which is capable of hybridizing under medium stringency conditions with (i) the nucleic acid sequence set forth in SEQ ID NO: 1 or (ii) its complementary strand;
(d) an allelic form of (b) or (c); and
(e) a fragment of (b), (c), or (d).

The present invention also relates to isolated nucleic acid sequences encoding the polypeptides and to nucleic acid constructs, vectors, and host cells comprising the nucleic acid sequences as well as methods for producing the polypeptides. The present invention further relates to composite feeds and methods of reducing phytate levels.

BRIEF DESCRIPTION OF THE FIGURES

FIG. 2 shows the genomic DNA sequence and deduced amino acid sequence of *Thermomyces lanuginosus* CBS 586.94 phytase (SEQ ID NO: 1 and SEQ ID NO:2, respectively).

FIG. 3 shows the alignment of the amino acid sequences for the phytases from *Thermomyces lanuginosus* CBS 586.94 and *Aspergillus niger* (ficuum) NRRL 3135 (SEQ ID NO:3).

FIG. 13 shows NMR spectra, showing the product profile of a *Aspergillus niger (ficuum)* phytase and a *Thermomyces lanuginosus* phytase, after twenty minutes.

DETAILED DESCRIPTION OF THE INVENTION

Polypeptides Having Phytase Activity

Figure 1:
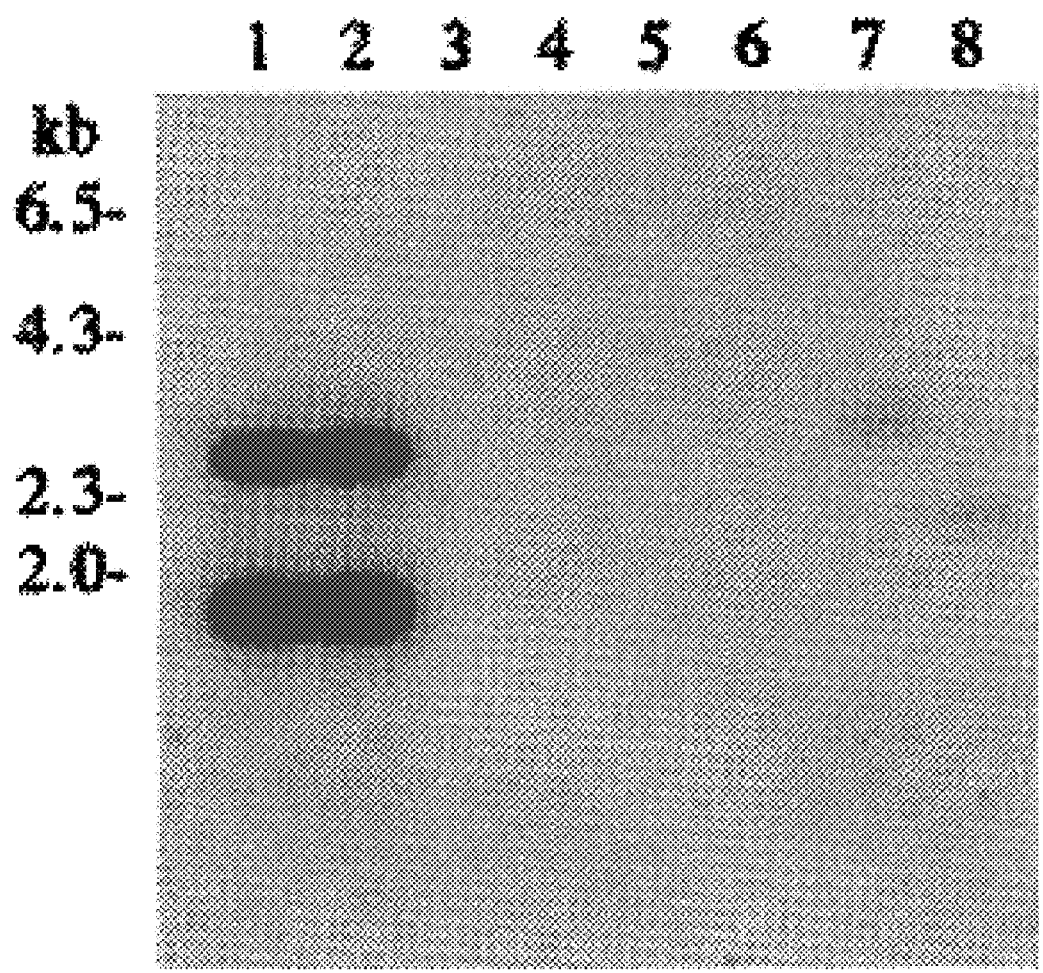
FIG. 1 shows an autoradiogram from Southern hybridization analysis of *Thermomyces lanuginosus* CBS 586.94 genomic DNA with a phytase gene probe.

In a first embodiment, the present invention relates to polypeptides which have 3,6-phytase activity. Thus, the polypeptides of this aspect of the invention belong to a novel class of phytases exhibiting high initial affinity for the 6- as well as the 3-position of phytic acid, in other words it is neither a 3-phytase nor a 6-phytase but less position specific than hitherto reported for any known phytase. Preferably, these polypeptides have a greater initial affinity for the 3-position than the 6-position. Moreover, these polypeptides are obtained from a fungal strain, more preferably a filamentous fungal strain. In a most preferred embodiment, the polypeptide is obtained from Thermomyces, more preferably *Thermomyces lanuginosus,* and most preferably the strain CBS 586.94.

In a second embodiment, the present invention relates to polypeptides which have an amino acid sequence which has a degree of identity to the amino acid sequence set forth in SEQ ID NO:2 of at least about 60%, preferably at least about 70%, more preferably at least about 80%, even more preferably at least about 90%, most preferably at least 95%, and even most preferably at least about 97%, which qualitatively retain the phytase activity of the polypeptides (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence set forth in SEQ ID NO:2. For purposes of the present invention, the degree of identity between two amino acid sequences is determined by the Clustal method (Higgins, 1989, *CABIOS* 5: 151–153) with an identity table, a gap penalty of 10, and a gap length penalty of 10.

The amino acid sequences of the homologous polypeptides differ from the amino acid sequence set forth in SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, e.g., by H. Neurath and R. L. Hill, 1979, *In, The Proteins,* Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a preferred embodiment, the present invention relates to isolated polypeptides having phytase activity with the amino acid sequence set forth in SEQ ID NO:2, and allelic forms and fragments thereof which retain phytase activity. Preferably, a fragment contains at least 400 amino acid residues, more preferably at least 425 amino acid residues, and most preferably at least 475 amino acid residues.

In a third embodiment, the present invention relates to isolated polypeptides having phytase activity which are encoded by nucleic acid sequences capable of hybridizing under high, medium, or low stringency conditions with an oligonucleotide probe which hybridizes under the same conditions with the nucleic acid sequence set forth in SEQ ID NO:1 or its complementary strand (J. Sambrook, E .F. Fritsch, and T. Maniatus, 1989, *Molecular Cloning, A Laboratory Manual,* 2d edition, Cold Spring Harbor, N.Y.), and allelic forms and fragments thereof. Hybridization indicates that the analogous nucleic acid sequence hybridizes to the oligonucleotide probe corresponding to the polypeptide encoding part of the nucleic acid sequence shown in SEQ ID NO:1, under low to high stringency conditions (for example, prehybridization and hybridization at 42° C. in 5×SSPE, 0.3% SDS, 200 mg/ml sheared and denatured salmon sperm DNA, and either 50, 35 or 25% formamide for high, medium and low stringencies, respectively), following standard Southern blotting procedures. The amino acid sequence set forth in SEQ ID NO:2 or a partial amino acid sequence thereof may be used to design an oligonucleotide probe, or a nucleic acid sequence encoding a polypeptide of the present invention, such as the nucleic acid sequence set forth in SEQ ID NO:1, or a subsequence thereof, may be used to identify and clone DNA encoding polypeptides having phytase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}P$, $^{3}H$, $^{35}S$, biotin, or avidin).

Thus, a genomic, cDNA or combinatorial chemical library prepared from such other organisms may be screened for DNA which hybridizes with the probes described above and which encodes a polypeptide having phytase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, the carrier material is used in a Southern blot in which the carrier material is finally washed three times for 30 minutes each using 2×SSC, 0.2% SDS at preferably not higher than 50° C., more preferably not higher than 55° C., even more preferably not higher than 60° C., and most preferably not higher than 65° C. Molecules to which the oligonucleotide probe hybridizes under these conditions are detected using X-ray film.

In a preferred embodiment, the isolated polypeptides of the present invention are encoded by nucleic acid sequences capable of hybridizing under medium stringency conditions with an oligonucleotide probe which hybridizes under the same conditions with the nucleic acid sequence set forth in SEQ ID NO: 1 or its complementary strand, and allelic forms and fragments thereof. In a more preferred embodiment. the isolated polypeptides of the present invention are encoded by nucleic acid sequences capable of hybridizing under high stringency conditions with an oligonucleotide probe which hybridizes under the same conditions with the nucleic acid sequence set forth in SEQ ID NO: 1 or its complementary strand, and allelic forms and fragments thereof.

The present invention also relates to polypeptides having immiunochemical identity or partial immunochemical identity to the polypeptide native to *Thermomyces lanuginosus* CBS 586.94. In this embodiment, a polypeptide of the present invention is used to produce antibodies which are immunoreactive or bind to epitopes of the polypeptide. A polypeptide having immunochemical identity to the polypeptide native to *Thermomyces lanuginosus* CBS 586–94 means that an antiserum containing antibodies against the polypeptide native to *Thermomyces lanuginosus* CBS 586.94 reacts with the other polypeptide in an identical fashion such as total fuision of precipitates, identical precipitate morphology, and/or identical electrophoretic mobility using a specific imimunochemical technique. A further explanation of immunochemical identity is described by Axelsen, Bock, and Krøll, In N. H. Axelsen, J. Krøll, and B. Weeks, editors, *A Manual of Quantitative Immunoelectrophoresis*, Blackwell Scientific Publications, 1973, Chapter 10. Partial immunochemical identity means that an antiserum containing antibodies against the polypeptide native to *Thermomyces lanuginosus* CBS 586.94 reacts with the other polypeptide in a partially identical fashion such as partial fusion of precipitates, partially identical precipitate morphology, and/or partially identical electrophoretic mobility using a specific immunochemical technique. A fuirther explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11. The inumunochemical properties are determined by immunological cross-reaction identity tests by the well-known Ouchterlony double immunodiffusion procedure. Specifically, an antiserum against the polypeptide of the invention is raised by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31).

Polypeptides which are encoded by nucleic acid sequences which are capable of hybridizing with an oligonucleotide probe which hybridizes with the nucleic acid sequence set forth in SEQ ID NO:1 or its complementary strand and allelic forms and fragments thereof, the homologous polypeptides and polypeptides having identical or partially identical immunological properties may be obtained from microorganisms of any genus. Preferably, they are obtained from a bacterial source. In another preferred embodiment, these polypeptides are obtained from a fungal source. Sources for such polypeptides are strains of the genus Thermomyces and species thereof available in public depositories. Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a cDNA library of another microorganism, in particular a fungus, such as a strain of an Aspergillus sp., in particular a strain of *Aspergillus aculeatus, Aspergillus awamori, Aspergillus foetidus, Aspergillus japonicus, Aspergillus nidulans, Aspergillus niger* or *Aspergillus oryzae,* a strain of Trichoderma sp., in particular a strain of *Trichoderma harzianum, Trichoderma koningii, Trichoderma longibrachiatum, Trichoderma reesei* or *Trichoderma viride,* or a strain of a Fusarium sp., in particular a strain of *Fusarium cerealis, Fusarium crookwellense, Fusarium graminearum, Fusarium oxysporum, Fusarium sambucinum, Fusarium sulphureum,* or *Fusarium venenatum,* or a strain of a Humicola sp., or a strain of an Aureobasidium sp., a Cryptococcus sp., a Filibasidium sp., a Magnaporthe sp., a Myceliophthora sp., a Neocallimastix sp., a Paecilomyces sp., a Piromyces sp., a Talaromyces sp., a Thermoascus sp., a Thielavia sp., or a Schizophyllum sp. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The polypeptides of the present invention are preferably obtained from species of Thermomyces including, but not limited to, *Thermomyces ibadanensis, Thermomyces lanuginosus, Thermomyces stellatus,* and *Thennomyces verrucosus.* Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

In a more preferred embodiment, a polypeptide of the present invention is obtained from *Thermomyces lanuginosus,* and most preferably from *Thermomyces lanuginosus* CBS 586.94 or a mutant strain thereof, e.g., the polypeptide with the amino acid sequence set forth in SEQ ID NO:2.

A polypeptide of the present invention may further be obtained from other fungi which are synonyms of Thermomyces as described by S. C. Jong, J. M. Birmingham, and G. Ma in *ATCC Names of Industrial Fungi,* American Type Culture Collection, Rockville, Md., 1994 or M. B. Ellis in *Dematiaceous Hyphomycetes,* Commonwealth Mycological Institute, Surrey, England, 1971. For example, synonyms of *Thermomyces lanuginosus* include *Acremoniella thermophila, Humicola lanuginosa, Monotospora lanuginosa,* and *Sepedonium lanuginosum*. The present invention also encompasses phytases obtained from fungi which are teleomorphs of Thermomyces. The genus Thermomyces is a terrestrial member of the group of dematiaceous hyphomycete fungi. Colonies are effuse, cottony or velvety, and grey, greenish grey, buff, dark blackish brown, or black. Mycelia are partly superficial, partly immersed. Conidiophores are micronematous or semi-macronematous, mononematous, unbranched or irregularly branched, straight or flexous, colorless or brown, and smooth. Conidiogenous cells are monoblastic, integrated and terminal or discrete, determinate, cylindrical or lageniform. Conidia are solitary, dry, acrogenous, simple, spherical to subspherical or angular and lobed, pale to dark blackish brown, smooth or verrucose, and O-septate. No phialidic state is known.

For purposes of the present invention, the term "obtained from" as used herein in connection with a given source shall mean that the polypeptide is produced by the source or by a cell in which a gene from the source has been inserted.

As defined herein, an "isolated" polypeptide is a polypeptide which is essentially free of other non-phytase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The polypeptides of the present invention are characterized as having a high activity at high temperatures. More specifically, these polypeptides have maximum phytase activity near 65° C. and partial activity even at 75° C. In contrast, the Aspergillus niger phytase is essentially inactive at 65° C.

Nucleic Acid Sequences

The present invention also relates to isolated nucleic acid sequences which encode a polypeptide of the present invention. In a preferred embodiment, the nucleic acid sequence encodes a polypeptide obtained from Thermozyces, e.g., *Thermomyces lanuginosus*, and in a more preferred embodiment, the nucleic acid sequence is obtained from *Thermomyces lanuginosus* CBS 586.94, e.g., the nucleic acid sequence set forth in SEQ ID NO:1. In a more preferred embodiment, the nucleic acid sequence is the sequence contained in plasmid pMWR46 which is contained in *Escherichia coli* NRRL B-21527. The present invention also encompasses nucleic acid sequences which encode a polypeptide having the amino acid sequence set forth in SEQ ID NO:2, which differ from SEQ ID NO: 1 by virtue of the degeneracy of the genetic code. The present invention also relates to subsequences of SEQ ID NO: 1 which encode a fragment of SEQ ID NO:2 which retains phytase activity. Preferably, a subsequence contains at least 1200 nucleotides, more preferably at least 1275 nucleotides, and most preferably at least 1425 nucleotides.

As described above, the nucleic acid sequences may be obtained from microorganisms which are synonyms or teleomorphs of Themonoyces as defined by M. B. Ellis, 1971, supra or Jong et al., 1994, supra.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application,* Academic Press, N.Y. Other nucleic acid amplification procedures such as ligase chain reaction (LCR), ligated activated transcription (LAT) and nucleic acid sequence-based amplification (NASBA) may be used. The nucleic acid sequence may be cloned from a strain of the Thermoryces producing the polypeptide, or another or related organism and thus, for example, may be an allelic or species variant of the polypeptide encoding region of the nucleic acid sequence.

The term "isolated" nucleic acid sequence as used herein refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a nucleic acid sequence which has a degree of identity to the nucleic acid sequence set forth in SEQ ID NO:1 of at least about 60%, preferably at least about 70%, more preferably at least about 80%, even more preferably at least about 90%, most preferably at least about 95%, and even most preferably at least about 97%, which encode an active polypeptide. For purposes of the present invention, the degree of identity between two nucleic acid sequences is determined by the Clustal method (Higgins, 1989, *CABIOS* 5: 151–153) with an identity table, a gap penalty of 10, and a gap length penalty of 10.

Modification of the nucleic acid sequence encoding the polypeptide may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO: 1, e.g., a sub-sequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2:95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244:1081–1085). In the latter technique mutations are introduced at every positively charged residue in the molecule, and the resultant mutant molecules are tested for phytase activity to identify amino acid residues that are critical to the activity of the molecule. Sites of substrate-enzyme interaction can also be determined by analysis of three-dimensional structure as determined by such techniques as nuclear magnetic resonance analysis, crystallography or photoaffinity labelling (see, e.g., de Vos et al., 1992, *Science* 255, 306–312; Smith et al., 1992, *Journal of Molecular Biology* 224:899–904; Wlodaver et al., 1992, *FEBS Letters* 309, 59–64).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

The present invention also relates to isolated polypeptides having phytase activity encoded by nucleic acid sequences which are capable of hybridizing under medium stringency conditions with an oligonucleotide probe which hybridizes under the same conditions with the nucleic acid sequence set forth in SEQ ID NO: 1 or its complementary strand (Sambrook et al., 1989, supra). Hybridization indicates that the analogous nucleic acid sequence hybridizes to the oligonucleotide probe corresponding to the polypeptide encoding part of the nucleic acid sequence shown in SEQ ID NO: 1 under standard conditions.

As disclosed earlier, the amino acid sequence set forth in SEQ ID NO:2 or a partial amino acid sequence thereof may be used to design an oligonucleotide probe, or a nucleic acid sequence encoding a polypeptide of the present invention, such as the nucleic acid sequence set forth in SEQ ID NO: 1, or a subsequence thereof can also be used as a probe, to isolate homologous genes of any genus or species.

Nucleic Acid Constructs

The present invention also relates to nucleic acid constructs comprising a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct may be synonymous with the term expression cassette when the nucleic acid construct contains all the control sequences required for expression of a coding sequence of the present invention. The term "coding sequence" as defined herein is a sequence which is transcribed into MRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothennophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroffetal., 1978, *Proceedings of the National Academy of Sciences USA* 75:3727–3731), as well as the tac promoter (DeBoer et al., 1983, *Proceedings of the National Academy of Sciences USA* 80:21–25). Further promoters are described in "Useful proteins from recombinant bacteria" in *Scientific American,* 1980, 242:74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase,

*Fusarium oxysporum* trypsin-like protease (as described in U.S. Pat. No. 4,288,627, which is incorporated herein by reference), and mutant, truncated, and hybrid promoters thereof. Particularly preferred promoters for use in filamentous fungal host cells are the TAKA amylase, NA2-tpi (a hybrid of the promoters from the genes encoding *Aspergillus niger* neutral a-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/ glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8:423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of a mRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15:5983–5990. Polyadenylation sequences are well known in the art for mammalian host cells.

The control sequence may also be a signal peptide coding region, which codes for an amino acid sequence linked to the amino terminus of the polypeptide which can direct the expressed polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to that portion of the coding sequence which encodes the secreted polypeptide. The foreign signal peptide coding region may be required where the coding sequence does not normally contain a signal peptide coding region. Alternatively, the foreign signal peptide coding region may simply replace the natural signal peptide coding region in order to obtain enhanced secretion of the phytase relative to the natural signal peptide coding region normally associated with the coding sequence. The signal peptide coding region may be obtained from a glucoamylase or an amylase gene from an Aspergillus species, a lipase or proteinase gene from a Rhizomucor species, the gene for the alpha-factor from *Saccharomyces cerevisiae,* an amylase or a protease gene from a Bacillus species, or the calf preprochymosin gene. However, any signal peptide coding region capable of directing the expressed phytase into the secretory pathway of a host cell of choice may be used in the present invention.

An effective signal peptide coding region for bacterial host cells is the signal peptide coding region obtained from the maltogenic amylase gene from Bacillus NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), and the Bacillus subtilis PrsA gene. Further signal peptides are described by Simonen and Palva, 1993, *Microbiological Reviews* 57:109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Useful signal peptides for yeast host cells are obtained from the genes for Saccharomyces cerevisiae a-factor and Saccharomyces cerevisiae invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophila* laccase gene (WO 95/33836).

The nucleic acid constructs of the present invention may also comprise one or more nucleic acid sequences which encode one or more factors that are advantageous in the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

An activator is a protein which activates transcription of a nucleic acid sequence encoding a polypeptide (Kudla et al., 1990, *EMBO Journal* 9: 1355–1364; Jarai and Buxton, 1994, *Current Genetics* 26: 2238–244; Verdier, 1990, *Yeast* 6: 271–297). The nucleic acid sequence encoding an activator may be obtained from the genes encoding *Bacillus stearothermophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further examples, see Verdier, 1990, supra and MacKenzie et al., 1993, *Journal of General Microbiology* 139: 2295–2307.

A chaperone is a protein which assists another polypeptide in folding properly (Hartl et al., 1994, *TIBS* 19: 20–25; Bergeron et al., 1994, *TIBS* 19: 124–128; Demolder et al., 1994, *Journal of Biotechnology* 32: 179–189; Craig, 1993, *Science* 260: 1902–1903; Gething and Sambrook, 1992, *Nature* 355: 33–45; Puig and Gilbert, 1994, *Journal of Biological Chemistry* 269: 7764–7771; Wang and Tsou, 1993, *The FASEB Journal* 7: 1515–11157; Robinson et al., 1994, *Bio/Technology* 1: 381–384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For farther examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, *Yeast* 10: 67–79; Fuller et al., 1989, *Proceedings of the National Academzy of Sciences USA* 86: 1434–1438; Julius et al., 1984, *Cell* 37: 1075–1089; Julius et al., 1983, *Cell* 32: 839–852). The nucleic acid sequence encoding a processing protease may be obtained from the genes encoding *Saccharomyces cerevisiae* dipeptidylaminopeptidase, *Saccharomyces cerevisiae* Kex2, and *Yarrowia lipolytica* dibasic processing endoprotease (xpr6).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG genes of *Aspergillus nidulans* or *Aspergillus oryzae* and the bar gene of *Streptomyces hygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli,* and pUB110, pE194, pTA1060, and pAMβ1 permitting replication in Bacillus. Examples of origin of replications for use in a yeast host cell are the 2 micron origin of replication, ARS 1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75:1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. Id: "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non- homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis;* or a Streptomyces cell, e.g., *Streptonzyces lividans* or *Streptomyces murinus,* or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. The transformation of a bacterial host cell may, for instance, be effected by protoplast transformation (see, e.g., Chang and Cohen, 1979, *Molecular General Genetics* 168:111–115), by using competent cells (see, e.g., Young and Spizizin, 1961, *Journal of Bacteriology* 81:823–829, or Dubnau and Davidoff-Abelson, 1971, *Journal of Molecular Biology* 56:209–221), by electroporation (see, e.g., Shigekawa and Dower, 1988, *Biotechniques* 6:742–751), or by conjugation (see, e.g., Koehler and Thome, 1987, *Journal of Bacteriology* 169:5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed below. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., *Saprolegniomycetous aquatic* fungi (water molds) such as Achlya. Examples of mitosporic fungi include Aspergillus, Penicillium, Candida, and Alternaria. Representative groups of Zygomycota include, e.g., Rhizopus and Mucor.

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharomyces), Nadsonioideae, Lipomycoideae, and Saccharomycoideae (e. g., genera Pichia, Kluyveromyces and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomiyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast,* Bacil, M., Horecker, B. J., and Stopani, A. O. M., editors, 2nd edition, 1987; *The Yeasts,* Rose, A. H., and Harrison, J. S., editors, 2nd edition, 1987; and *The Molecular Biology of the Yeast Saccharomyces,* Strathern et al., editors, 1981).

In a more preferred embodiment, the yeast host cell is a cell of a species of Candida, Kluyveromyces, Saccharomyces, Schizosaccharomyces, Pichia, or Yarrowia.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharonzyces oviformis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more preferred embodiment, the filamentous fungal host cell is a Myceliophthora cell. In another even more preferred embodiment, the filamentous fungal host cell is a Neurospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypocladium cell. In another even more preferred embodiment, the filamentous fungal host cell is a Trichoderma cell.

In a most preferred embodiment, the filamentous fungal host cell is an *Aspergillus awamori, Aspergillusfoetidus, Aspergillusjaponicus, Aspergillus niger* or *Aspergillus oryzae* cell. In another most preferred embodiment, the filamentous fungal host cell is a *Fusarium cerealis, Fusarium crookwellense, Fusarium graminearum, Fusarium oxysporum, Fusarium sambucinum, Fusarium sulphureum,* or *Fusarium venenatum* cell. In another most preferred embodiment, the filamentous fungal host cell is a *Humicola insolens* or *Humicola lanuginosa* cell. In another most preferred embodiment, the filamentous fungal host cell is a *Mucor miehei* cell. In another most preferred embodiment, the filamentous fungal host cell is a *Myceliophthora thermophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderma reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81:1470–1474. A suitable method of transforming Fusarium species is described by Malardier et al., 1989, *Gene* 78:147–156 or in copending U.S. Ser. No. 08/269,449. Yeast may be transformed using the procedures described by Becker and Guarente, In Abelson, J. N. and Simon, M. I., editors, *Guide to Yeast Genetics and Molecular Biology,* Methods in Enzymology, Volume 194, pp 182–187, Academic Press, Inc., New York; Ito et al., 1983, *Journal of Bacteriology* 153:163; and Hinnen et al., 1978, *Proceedings of the National Academy of Sciences USA* 75:1920. Mammalian cells may be transformed by direct uptake using the calcium phosphate precipitation method of Graham and Van der Eb (1978, *Virology* 52:546).

Methods of Production

The present invention also relates to methods for producing a polypeptide of the present invention comprising (a) cultivating a Thermomzyces strain to produce a supernatant comprising the polypeptide; and (b) recovering the polypeptide.

The present invention also relates to methods for producing a polypeptide of the present invention comprising (a) cultivating a host cell under conditions conducive to expression of the polypeptide; and (b) recovering the polypeptide.

In both methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi,* Academic Press, Calif., 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining phytase activity are known in the art and include, e.g., the assay of inorganic phosphate liberated from phytic acid.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation. The recovered polypeptide may then be further purified by a variety of chromatographic procedures, e.g., ion exchange chromatography, gel filtration chromatography, affinity chromatography, or the like.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., *Protein Purification*, J. -C. Janson and Lars Ryden, editors, VCH Publishers, New York, 1989).

Polypeptide Compositions

In a still further aspect, the present invention relates to polypeptide compositions which are enriched in a polypeptide of the present invention. In the present context, the term "enriched" is intended to indicate that the phytase activity of the polypeptide composition has been increased, e.g., with an enrichment factor of 1.1, conveniently due to addition of a polypeptide of the invention.

The polypeptide composition may be one which comprises a polypeptide of the invention as the major enzymatic component, e.g., a mono-component polypeptide composition. Alternatively, the composition may comprise multiple enzymatic activities, such as an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peroxidase, a phytase, a polyphenoloxidase, a proteolytic enzyme, a ribonuclease, or a xylanase. The additional enzyme(s) may be producible by means of a microorganism belonging to the genus Aspergillus, preferably *Aspergillus aculeatus, Aspergillus awamori, Aspergillus niger,* or *Aspergillus oryzae,* or Trichodenna, Humicola, preferably *Humicola insolens,* or Fusarium, preferably *Fusarium cerealis, Fusarium crookwellense, Fusarium graminearum, Fusarium oxysporum, Fusarium sambucinum, Fusarium sulphureum,* or *Fusarium venenatum.*

The polypeptide compositions may be prepared in accordance with methods known in the art and may be in the form of a liquid or a dry composition. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention also relates generally to the use of the polypeptide of the present invention for catalyzing the liberation of inorganic phosphate from phytate or phytic acid.

More specifically, the polypeptides may be used in human food or animal feed compositions or as additives for such preparations, wherein the phytase improves digestibility, promotes growth, and improves food and feed utilization or its conversion efficiency.

A "feed composition" and a "food composition," respectively, means any natural or artificial diet, meal or the like or components of such meals intended or suitable for being eaten, taken in, digested, by an animal and a human being, respectively.

A "food or feed additive" is an essentially pure compound or a multi component composition intended for or suitable for being added to food or feed. It usually comprises one or more compounds such as vitamins, minerals or feed enhancing enzymes and suitable carriers and/or excipients, and it is usually provided in a form that is suitable for being added to animal feed.

The invention also relates to feed and food compositions and additives therefore comprising a polypeptide of the invention.

An effective amount of the polypeptide in food or feed is from about 10–20,000; preferably from about 10 to 15,000, more preferably from about 10 to 10,000, in particular from about 100 to 5,000, especially from about 100 to about 2,000 U/kg feed or food.

The invention also relates to a method for reducing phytate levels in animal manure, comprising feeding an animal a feed comprising an effective amount of a polypeptide of the invention.

Also within the scope of the invention is the use of a polypeptide of the invention during the preparation of food or feed preparations or additives, i.e., the polypeptide exerts its phytase activity during the manufacture only and is not active in the final food or feed product. This aspect is relevant for instance in baking.

The present invention also relates to the use of the polypeptides in methods for liquefying a starch, comprising (a) treating the starch with a polypeptide of claim 1 prior to or simultaneously with liquefying; (b) adding an et-amylase to the starch; and (c) reacting the starch of step (b) for a time and at a temperature effective to liquefy the starch. In this process, the polypeptide catalyzes the hydrolysis of phytate associated with the starch.

The present invention also relates to a transgenic plants and plant parts such as plant seeds, and plant cells, which have been transformed with a DNA sequence encoding the polypeptide of the invention so as to express or produce this enzyme. The present invention also relates to compositions and uses of such plants and plant parts, especially as feed and food or additives therefore.

The transgenic plants can be dicotyledonous or monocotyledonous, for short a dicot or a monocot. Of primary interest are such plants which are potential food or feed components and which comprise phytic acid. A normal phytic acid level of feed components is 0.1–100 g/kg, or more usually 0.5–50 g/kg, most usually 0.5–20 g/kg. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are legumes, such as lupins, pea, bean and soybean, and cruciferous (family Brassicaceae), such as cauliflower, oil seed rape and the closely related model organism *Arabidopsis thaliana.*

Such transgenic plants, plant parts and plant cells are capable of degrading their own phytic acid, and accordingly the need for adding such enzymes to food or feed comprising such plants is alleviated. Preferably, the plants and plant parts, e.g. the seeds, are ground or milled, and possibly also soaked before being added to the food or feed or before the use, e.g. intake, thereof, with a view to adapting the speed of the enzymatic degradation to the actual use.

If desired, the plant-produced polypeptide can also be recovered from the plant. In certain cases the recovery from the plant is to be preferred with a view to securing a heat stable formulation in a potential subsequent pelleting process.

Examples of plant parts are stem, callus, leaves, root, fruits, seeds, tubers etc. But also any plant tissue is included in this definition.

The present invention also relates to the progeny of such plants, plant parts and plant cells.

One skilled in the art will know how to construct a DNA expression construct for insertion into the plant in question, paying regard i.a. to whether the enzyme should be excreted in a tissue specific way. Of relevance for this evaluation is the stability (pH-stability, degradability by endogenous proteases etc.) of the phytase in the expression compartments of the plant. He will also be able to select appropriate regulatory sequences such as promoter and terminator sequences, and signal or transit sequences if required (Tague et al., 1988, *Plant Phys.* 86:506).

The plants, plant parts and plant cells can be transformed with this DNA construct using any known method. An example of such method is the transformation by a viral or bacterial vector such as bacterial species of the genus Agrobacterium genetically engineered to comprise the gene encoding the phytase of the invention. In addition, methods of directly introducing the phytase DNA into the plant cell or plant tissue are known in the art, e.g., micro injection and electroporation (Gasser et al., *Science* 244: 1293; Potrykus, 1990, *Bio/Techn.* 8: 535; Shimamoto et al., 1989, *Nature* 338: 274).

Following the transformation, the transformants are screened using any method known to the skilled man, following which they are regenerated into whole plants.

These plants, plant parts and plant cells as well as their progeny then carry the phytase encoding DNA as a part of their genetic equipment.

*Agrobacterium tumefaciens* mediated gene transfer is the method of choice for generating transgenic dicots (for review Hooykas & Schilperoort, 1992, *Plant Mol. Biol.* 19: 15–38). Due to host range limitations it is generally not possible to transform monocots with the help of *A. tumefaciens*. Here, other methods have to be employed. The method of choice for generating transgenic monocots is particle bombardment (microscopic gold or tungsten particles coated with the tranforming DNA) of embryonic calli or developing embryos (Christou, 1992, *Plant J.* 2: 275–281; Shimamoto, 1994, *Curr. Opin. Biotechnol.* 5: 158–162; Vasil et al., 1992, *Bio/Technology* 10: 667–674).

Also other systems for the delivery of free DNA into these plants, including viral vectors (Joshi & Joshi, 1991. *FEBS Lett.* 281: 1–8), protoplast transformation via polyethylene glycol or electroporation (for review see Potyrkus, 1991, *Annu. Rev. Plant Physiol. Plant Mol. Biol.* 42: 205–225), microinjection of DNA into mesophyll protoplasts (Crossway et al., 1986, *Mol. Gen. Genet.* 202: 79–85), and macroinjection of DNA into young floral tillers of cereal plants (de la Pena et al., 1987, *Nature* 325: 274–276) are preferred methods.

In general, the cDNA or gene encoding the phytase of the invention is placed in an expression cassette (e.g., Pietrzak et al., 1986, *Nucleic Acids Res.* 14: 5857–5868) consisting of a suitable promotor active in the target plant and a suitable terminator (termination of transcription). This cassette (of course including a suitable selection marker, see below) will be transformed into the plant as such in case of monocots via particle bombardment. In case of dicots the expression cassette is placed first into a suitable vector providing the T-DNA borders and a suitable selection marker which in turn are transformed into *Agrobacterium tumefaciens*. Dicots will be transformed via the Agrobacterium harbouring the expressioncassette and selection marker flanked by T-DNA following standard protocols (e.g. Akama et al., 1992, *Plant Cell Reports* 12: 7–11). The transfer of T-DNA from Agrobacterium to the Plant cell has been recently reviewed (Zupan & Zambryski, 1995, *Plant Physiol.* 107: 1041–1047). Vectors for plant transformation via Agrobacterium are commercially available or can be obtained from many labs that construct such vectors (e.g., Deblaere et al., 1985, *Nucleic Acids Res.* 13: 4777–4788; for review see Klee et al., 1987, *Annu. Rev. Plant Physiol.* 38: 467–486).

Available plant promoters: Depending on the process under manipulation, organ- and/or cell-specific expression as well as appropriate developmental and environmental control may be required. For instance, it is desirable to express a phytase cDNA in maize endosperm etc. The most commonly used promotor has been the constitutive 35S-CaMV promotor Franck et al., 1980, *Cell* 21: 285–294). Expression will be more or less equal throughout the whole plant. This promotor has been used successfully to engineer herbicide- and pathogen-resistant plants (for review see Stitt & Sonnewald, 1995, *Annu. Rev. Plant Physiol. Plant Mol. Biol.* 46: 341–368). Organ-specific promoters have been reported for storage sink tissues such as seeds, potato tubers, and fruits (Edwards & Coruzzi, 1990, *Annu. Rev. Genet.* 24: 275–303), and for metabolic sink tissues such as meristems (Ito et al., 1994, *Plant Mol. Biol.* 24: 863–878).

The present invention also relates to the use of a phytase of the invention during the preparation of food or feed preparations or additives, i.e. the phytase exerts its phytase activity during the manufacture only and is not active in the final food or feed product. This embodiment applies to dough making and baking.

The present invention is further described by the following examples which should not be construed as limiting the scope of the invention.

EXAMPLES

Example 1

*Thermomyces lanuginosus* CBS 586.94 Genomnic DNA Extraction

*Thermomyces lanuginosus* CBS 586.94 was grown in 25 ml of 0.5% yeast extract-2% glucose (YEG) medium for 24 hours at 32° C. and 250 rpm. Mycelia were then collected by filtration through MIRACLOTH (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to ensure mixing, and extracted twice with an equal volume of phenol:chloroform:isoamyl alcohol (25:24:1 v/v/v). Sodium acetate (3 M solution) was added to give a final concentration of 0.3 M and the nucleic acids were precipitated with 2.5 volumes of ice cold ethanol. The tube was centrifuged at 15,000×g for 30 minutes and the pellet was allowed to air dry for 30 minutes before resuspension in 0.5 ml of TE buffer. DNase-free ribonuclease A was added to a concentration of 100 μg/ml and the mixture was incubated at 37° C. for 30 min. Proteinase K (200 μg/ml) was then added and the mixture was incubated an additional hour at 37° C. Finally, the mixture was extracted twice with phenol:chloroform: isoamyl alcohol (25:24:1 v/v/v) before precipitating the DNA with sodium acetate and ethanol. The DNA pellet was dried under vacuum, resuspended in TE buffer, and stored at 4° C.

Example 2
Hybridization Analysis of Genomic DNA

The total cellular DNA sample prepared as described in Example 1 was analyzed by Southern hybridization (Maniatis et al., 1982, *Molecular Cloning, A Laboratory Manual*, Cold Spring Harbor Press, Cold Spring Harbor, N.Y.). Approximately 5 µg of the DNA sample were digested with BamHI or PstI and fractionated by size on a 1% agarose gel. The gel was photographed under short wavelength UV light and soaked for 15 minutes in 0.5 M NaOH-1.5 M NaCl followed by 15 minutes in 1 M Tris-HCl pH 8–1.5 M NaCl. DNA in the gel was transferred onto a Nytran™ hybridization membrane (Schleicher & Schuell, Keene, N.H.) by capillary blotting in 20×SSPE (3 M sodium chloride-0.2 M sodium dibasic phosphate-0.02 M disodium EDTA) according to Davis et al. (1980, Advanced Bacterial Genetics, A Manual for Genetic Engineering, Cold Spring Harbor Press, Cold Spring Harbor, N.Y.). The membrane was baked for 2 hours at 80° C. under vacuum and was soaked for 2 hours in the following hybridization buffer at 45° C. with gentle agitation: 5×SSPE, 25% formamide (v/v), 0.3% SDS, and 200 µg/ml denatured and sheared salmon testes DNA. A phytase-specific probe fragment (approximately 1.6 kb) was radiolabeted by nick translation (Maniatis et al., 1982, supra) with $\alpha[^{32}P]dCTP$ (Amersham, Arlington Heights, Ill.) and added to the hybridization buffer at an activity of approximately $1 \times 10^6$ cpm per ml of buffer. The mixture was incubated with the membrane overnight at 45° C. in a shaking water bath. Following incubation, the membrane was washed once in 1.0×SSPE with 0.1% SDS at 45° C. followed by two washes in 1.0×SSPE (no SDS) at the same temperature. The membrane was dried on a paper towel for 15 minutes, then wrapped in SARAN-WRAP™ and exposed to X-ray film overnight at −70° C. with intensifying screens (Kodak, Rochester, N.Y.).

Southern blotting indicates that the probe can be used as a probe to identify and clone the phytase gene from *Thermomzyces lanuginosus* CBS 586.94 as shown in FIG. 1.

Example 3
DNA Libraries and Identification of Phytase Clones

Genomic DNA libraries were constructed using the bacteriophage cloning vector λZipLox (Life Technologies, Gaithersburg, Md.) with *E. coli* Y1090ZL cells (Life Technologies, Gaithersburg, Md.) as a host for plating and purification of recombinant bacteriophage and *E. Coli* DH10Bzip (Life Technologies, Gaithersburg, Md.) for excision of individual pZL1-phytase clones. Total cellular DNA was partially digested with Tsp509I and size-fractionated on 1% agarose gels. DNA fragments migrating in the size range 3–7 kb were excised and eluted from the gel using Prep-a-Gene reagents (BioRad Laboratories, Hercules, Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *E. coli* Y1090ZL cells (Life Technologies, Gaithersburg, Md.). Approximately 30,000 plaques from the library were screened by plaque-hybridization with the radiolabeled phytase probe described in Example 2. One positive clone which hybridizes strongly to the probe was picked and purified twice in *E. coli* Y1090ZL cells. The phytase clone was subsequently excised from the λZipLox vector as pZL1-phytase clones (D'Alessio et al., 1992, Focus® 14: 76) yielding *E. coli* DH5α (pMWR46).

Example 4
DNA Sequencing of *Thermomyces lanuginosus* CBS 586.94 Phytase Gene

Restriction mapping of the pZL1-phytase clone *E. coli* DH5α (pMWR46) described in Example 3 was performed using standard methods (Maniatis et al., 1982, supra). DNA sequencing of the phytase clones was performed with an Applied Biosystems Model 373A Automated DNA Sequencer (Applied Biosystems, Inc., Foster City, Calif.) using the primer walking technique with dye-terminator chemistry (Giesecke et al., 1992, *Journal of Virol. Methods* 38: 47–60). In addition to the lac-forward and lac-reverse primers, specific oligonucleotide sequencing primers were synthesized on an Applied Biosystems Model 394 DNA/RNA Synthesizer (Applied Biosystems, Inc., Foster City, Calif.) according to the manufacturer's instructions.

Example 5
Properties of the *Thermomyces lanuginosus* CBS 586.94 Phytase Gene

DNA sequencing of a portion of a cloned *Thermomyces lanuginosus* CBS 586.94 phytase gene (*E. coli* DH5α-pMWR46) demonstrated an open reading frame (SEQ ID NO: 1) (FIG. 2) with homology to the *Aspergillus niger* (*ficuum*) NRRL 3135 phytase gene (FIG. 3).

The positions of introns and exons within the *Thermomyces lanuginosus* CBS 586.94 phytase gene were assigned based on alignments of the deduced amino acid sequence to the deduced amino acid sequence of the corresponding *Aspergillus niger* (*ficuum*) NRRL 3135 phytase gene product. On the basis of this comparison, the *Thermomyces lanuginosus* CBS 586.94 phytase gene is comprised of 2 exons (47 and 1377 bp) which are interrupted by 1 small intron (55 bp). The size and composition of the intron is consistent with those of other fungal genes (Gurr et al., 1987, In Kinghorn, J. R. (ed.), *Gene Structure in Eukaryotic Microbes*, pp. 93–139, IRL Press, Oxford) in that all contain consensus splice donor and acceptor sequences as well as the consensus lariat sequence (PuCTPuAC) near the 3' end of each intervening sequence.

The deduced amino acid sequence of the *Thermomoyces lanuginosus* CBS 586.94 gene product is shown in FIG. 2 (SEQ ID NO:2). Based on the rules of von Heijne (1984, *Journal of Molecular Biology* 173: 243–251), the first 22 amino acids of the *Thermomyces lanuginosus* gene product likely comprise a secretory signal peptide which directs the nascent polypeptide into the endoplasmic reticulum. The mature phytase is an acidic protein (predicted isoelectric point=5.4) composed of 453 amino acids (MW=51 kDa). The deduced amino acid sequence contains the active site motif RHGXRXP (SEQ ID NO:2) which is shared by other known fungal phytases (Ullah and Dischinger, 1993, *Biochem. Biophys. Res. Commun.* 192: 754–759).

The deduced amino acid sequence of the mature *Thermomyces lanuginosus* CBS 586.94 phytase shares approximately 47.5% identity with the phytase from *Aspergillus niger* (*ficuum*) NRRL 3135 as shown in FIG. 3 (SEQ ID NO:3).

Example 6

Cross-Hybridization Studies Using Genomic DNA from Other Fungi

The cloned *Thermomyces lanuginosus* CBS 586.94 phytase gene was used as a probe in Southern hybridization experiments with genomic DNA samples from a variety of fungal genera. Southern blots were probed under conditions of low stringency (25% formamide, 5×SSPE, 0.3% SDS at 42° C.) and medium stringency (35% formamide, 5×SSPE, 0.3% SDS at 42° C.). Genomic DNA samples were isolated from the following species using the protocol outlined in Example 1: *Corynascus thermophilus* (ATCC 22066), *Fusarium graminearum* (ATCC 20334), *Humicola grisea* var. *thermoidea* (ATCC 16453), *Neurospora crassa* (FGSC 987), *Botrytis cinerea* (ATCC 11542), *Curvularia verruculosa* (CBS 147.63), *Rhizoctonia solani* (IMI 358730) *Trichoderma harzianum* (CBS 819.68), *Absidia sporophora-variabilis* (ATCC 36019), *Myceliophthora thermophila* (CBS 117.65), and *Penicillium diversum* (CBS 320.48). Each DNA sample (ca. 5 μg) was digested with BamHI prior to electrophoresis on a 1% agarose gel. The DNA was blotted to Zeta-Probe nylon membrane (BioRad Laboratories, Hercules, Calif.) and probed with a nick translated DNA probe comprising the phy1 gene. The blots were washed with 2×SSPE±0.1% SDS at 42° C. The phytase gene from *Thermomyces lanuginosus* CBS 586.94 cross-hybridized with probable phytase gene sequences in several other fungal species (Table 1). Under conditions of low stringency strong hybridization signals were apparent in DNAs from *Corynascus thermophilus, Fusarium graminearum, Humicola grisea* var. *thermoidea, Neurospora crassa* and, of course, *Thermomyces lanuginosus*. Weaker signals were detected in *Botrytis cinerea, Curvulania verruculosa, Rhizoctonia solani,* and *Trichoderma harzianum.* No hybridization was detected in *Absidia sporophora-variabilis, Myceliophthora thermophila,* or *Penicillium diversum.* Using medium stringency, strong hybridization signals were visible with only *Corynascus thermophilus, Fusarium graminearum,* and *Thermomyces lanuginosus.* Weak hybridization was observed with DNAs from *Humicola grisea* var. *thermoidea* and *Neurospora crassa.* These data indicate that the *Thermomyces lanuginosus* CBS 586.94 phytase gene can be used as a probe to clone phytase genes from other filamentous fungi.

TABLE 1

Hybridization of genomic DNA samples from various fungi probed with the cloned *Thermomyces lanuginosus* phytase gene. A +++ denotes a strong positive hybridization signal, + denotes a weak signal, and, − denotes no detectable hybridization.

| Genomic DNA source | Low Stringency | High Stringency |
|---|---|---|
| *Absidia sporphora-variabilis* | − | − |
| *Botrytis cinerea* | + | − |
| *Corynascus thermophilus* | +++ | +++ |
| *Curvularia verruculosa* | + | − |
| *Fusarium graminearum* | +++ | +++ |
| *Humicola grisea* var. *thermoidea* | +++ | + |
| *Myceliophthora thermophila* | − | − |
| *Neurospora crassa* | +++ | + |
| *Penicillium diversum* | − | − |
| *Rhizoctonia solani* | + | − |
| *Thermomyces lanuginosus* | +++ | +++ |
| *Trichoderma harzianum* | + | − |

Example 7

Construction of the Phytase Expression Vector pMWR48

Two synthetic oligonucleotide primers shown below were designed to PCR amplify the *Thermomyces lanuginosus* CBS 586.94 phytase gene coding sequence from plasmid pMWR46 (*E. coli* DH5ce-pMWR46) for subcloning and expression in a Fusarium host. Forward primer: 5'-ATTTAAATGGCGGGGATAGGTTTGG-3' (SEQ ID NO:4) Reverse primer: 5'-CTTAATTAATCAAAAGCAGCGATCCC-3' (SEQ ID NO:5) The sense primer was designed to the first in-frame ATG and extends 14 bp downstream. The antisense primer was designed to a region 14 bp upstream of the translational stop codon and extends through the stop codon.

Figure 4:
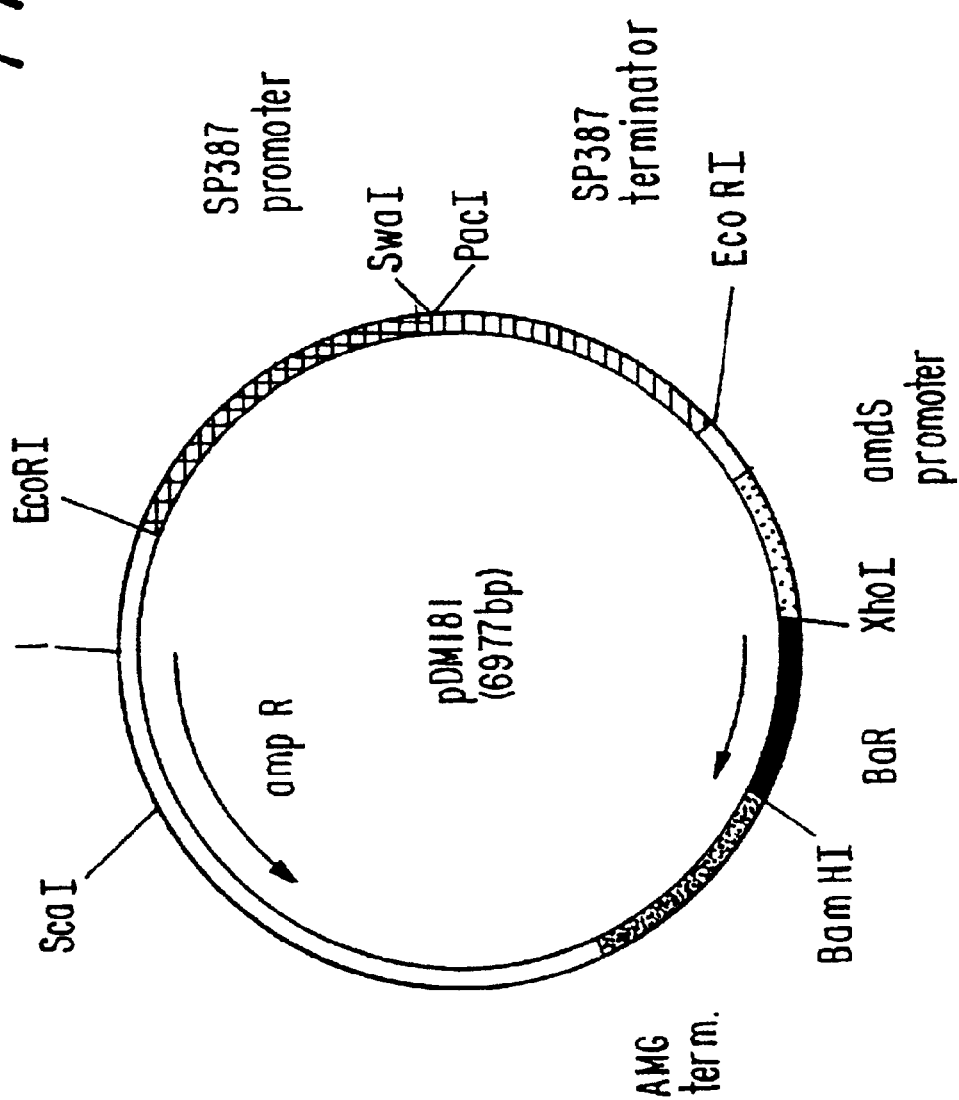
FIG. 4 shows a restriction map of pDM181.

In order to facilitate the subcloning of the gene fragment into an expression vector designated pDM181 (FIG. 4), SwaI and PacI restriction enzyme sites were introduced at the 5' and 3' end of the phytase gene, respectively. The vector pDM181 contained the Fusafium oxysporum trypsin-like protease promoter and terminator (WO 96/00787) as regulatory sequences. The plasmid also contained the bar gene as a selectable marker for fungal transformations (de Block et al., 1987, *EMBO Journal* 6:2513–2518).

Figure 5:
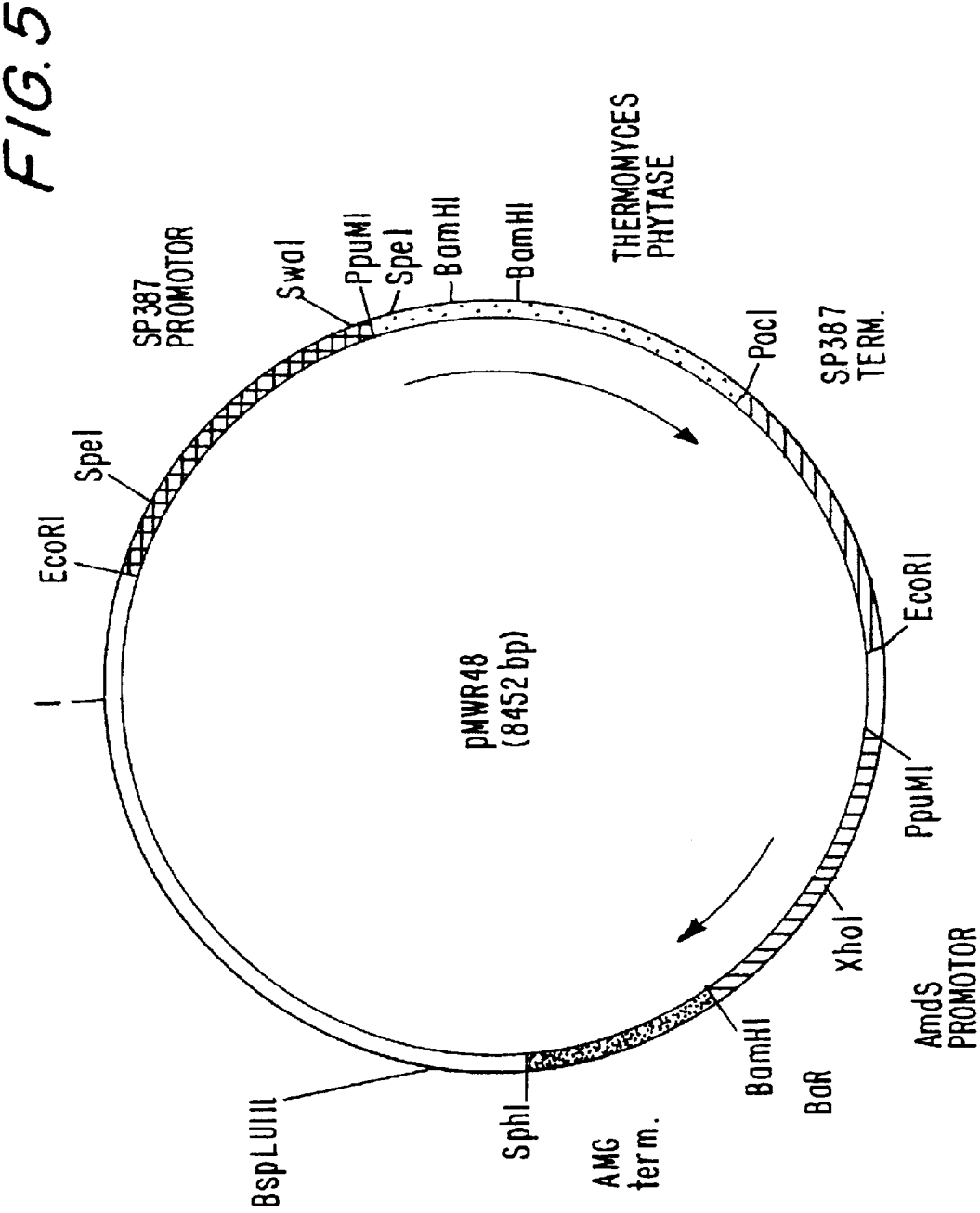
FIG. 5 shows a restriction map of pMWR48.

One hundred picomoles of each of the primers above were used in a PCR reaction i-containing 52 ng of pEJG13, 1×Pwo Buffer (Boehringer Mannheim, Indianapolis, Ind.), 1 mM each dATP, dTTP, dGTP, and dCTP, and 2.5 units of PwoI (Boehringer Mannheim, Indianapolis, Ind.). The amplification conditions were one cycle at 94° C. for 2 minutes, 50° C. for 30 seconds, and 72° C. for 1 minute; 9 cycles each at 94° C. for 15 seconds, 50° C. for 30 seconds, and 72° C. for 1 minute; 15 cycles each at 94° C. for 15 seconds, 55° C. for 30 seconds, and 72° C. for 1 minute plus 20 seconds for each additional cycle; one cycle at 94° C. for 15 seconds, 55° C. for 30 seconds, and 72° C. for 7 minutes; and a soak cycle at 43° C. The amplified 2866 bp DNA fragment was purified by gel electrophoresis and cut with restriction endonucleases SwaI and PacI (using conditions specified by the manufacturer). The cut fragment was cloned into pDM181 (FIG. 4) that had been previously cut with SwaI and PacI resulting in the expression plasmid pMWR48 (FIG. 5) in which transcription of the phytase gene was under the control of the *Fusarium oxysporum* trypsin-like protease promoter. The plasmid pMWR48 was transformed into *E. coli* DH5α cells. The *E. coli* transformant containing the pMWR48 plasmid was isolated and plasmid DNA was prepared according to procedures described by Sambrook et al., 1989, supra.

Example 8

Transformation of Fusafium CC1-3 and Analysis of Transformants

Fusarium strain CC1-3, a highly branched morphological mutant of Fusarium strain A3/5 (ATCC 20334) (Wiebe et al., 1992, *Mycological Research* 96: 555–562; Wiebe et al., 1991, *Mycological Research* 95: 1284–1288; Wiebe et al., 1991, *Mycological Research* 96: 555–562), was grown in a liquid medium containing Vogel's salts, (Vogel, 1964, *Am. Nature* 98: 435446), 25 mM $NaNO_3$, and 1.5% glucose for 4 days at 28° C. and 150 rpm. Conidia were purified by filtration through 4 layers of cheesecloth and fmally through one layer of MIRACLOTH™. Conidial suspensions were concentrated by centrifugation. Fifty ml of YPG medium comprised of 1% yeast extract, 2% bactopeptone, and 2% glucose were inoculated with approximately $10^8$ conidia, and incubated for 14 hours at 24° C. and 150 rpm. Resulting hyphae were trapped on a sterile 0.4 μm filter and washed successively with sterile distilled water and 1.0 M $MgSO_4$. The hyphae were resuspended in 10 ml of NOVOZYM 234™ solution (2–10 mg/ml in 1.0 M $MgSO_4$) and digested for 15–30 minutes at 34° C. with agitation at 80 rpm. Undigested hyphal material was removed from the resulting protoplast suspension by successive filtration through 4 layers of cheesecloth and through MIRACLOTH™. Twenty ml of 1 M sorbitol were combined with the protoplast solution. After mixing, the protoplasts were pelleted by centrifugation and washed successively by resuspension and centrifugation in 20 ml of 1 M sorbitol and in 20 ml of STC (0.8 M sorbitol, 0.05 M Tris pH 8.0, 0.05 M $CaCl_2$). The washed protoplasts were resuspended in 4 parts STC and 1 part SPTC (0.8 M sorbitol, 40% PEG 4000, 0.05 M Tris pH 8.0, 0.05 M $CaCl_2$) at a concentration of $5\times10^7$/ml. One hundred μl of protoplast suspension were added to 5 μg of pMWR48 in polypropylene tubes (17×100 mm), mixed and incubated on ice for 30 minutes. One ml of SPTC was mixed gently into the protoplast suspension and incubation was continued at room temperature for 20 minutes. 12.5 ml of molten solution (cooled to 40° C.) consisting of 1×Vogel's salts, 25 mM $NaNO_3$, 0.8 M sucrose and 1% low melting agarose (Sigma Chemical Company, St. Louis, Mont.) were mixed with the protoplasts and then plated onto an empty 100 mm Petri plate. Incubation was continued at room temperature for 10 to 14 days. After incubation at room temperature for 24 hours, 12.5 ml of the identical medium plus 10 mg of basta (Hoechst Schering, Rodovre, Denmark) per ml were overlayed onto the Petri plate. Basta was extracted twice with phenol:chloroform:isoamyl alcohol (25:24:1), and once with chloroform:isoamyl alcohol (24:1) before use. After two weeks, 17 transformants were apparent. A mycelial fragment from the edge of each transformant was transferred to individual wells of a 24 well plate containing Vogel's/BASTA medium. The medium contained 25 g of sucrose, 25 g of Noble agar, 20 ml of 50×Vogel's salts (Vogel, 1964, supra), 25 mM $NaNO_3$, and 10 g of basta per liter. The plate was sealed in a plastic bag to maintain moisture and incubated approximately one week at room temperature.

Example 9
Expression of *Thermomyces lanuginosus* CBS 586.94 Phytase Gene

A mycelial fragment from each of the 17 Fusarium CC1-3 transformants described in Example 8 was inoculated into 20 ml of M40ODa medium containing 50 g of maltodextrin, 2.0 g of $MgSO_4$-$7H_2O$, 2.0 g of $KH_2PO_4$, 4.0 g of citric acid, 8.0 g of yeast extract, 2.0 g of urea, and 0.5 ml of trace metals solution per liter and incubated for 7 days at 30° C. and 150 rpm. The medium was adjusted to pH 6.0 with 5 N NaOH. The trace metals solution contained 14.3 g of $ZnSO_4$-$7H_2O$, 2.5 g of $CuSO_4$-$5H_2O$, 0.5 g of $NiCl_2$-$6H_2O$, 13.8 g of $FeSO_4$-$7H_2O$, 8.5 g of $MnSO_4$-$H_2O$, and 3.0 g of citric acid per liter. The untransformed host was also run as a control. One ml of culture supernatant was harvested at 4, 5, and 7 days and stored at 4° C. Phytase activity was determined as described below.

A sample was diluted in 0.2 M citrate pH 5.5 buffer and 1 ml of the diluted sample was added to each of two test tubes. Two milliliters of 15% trichloroacetic acid (TCA) were added to one tube, while the other tube was pre-incubated at 40° C. for 5 min. One milliliter of 1% phytate substrate solution in 0.2 M citrate pH 5.5 buffer was subsequently added to both tubes. Samples lacking TCA were incubated at 40° C. for 30 minutes. At the end of the incubation period; 2 ml of TCA were added and the samples were allowed to cool. A volume of 100 microliters of each sample was then diluted to 1 ml in water and pre-incubated at 50° C. for 5 minutes. One milliliter of a reagent containing 1:2:1:1 of 6 N sulfuric acid:water:2.5% ammonium molybdate: 10% ascorbic acid was added to each sample and the samples were incubated another 15 minutes for color development. The resulting color was measured at 690 nm on a Molecular Devices Thernomax Microplate Reader (Molecular Devices, Sunnyvale, Calif.).

Spores from primary transformants producing the highest phytase activity were generated by inoculating 20 ml of a medium containing per liter 12.1 g of $NaNO_3$, 50 g of succinic acid, and 20 ml of 50×Vogel's salts (adjusted to pH 6.0) with mycelia and incubating at 30° C. with shaking for 2–3 days. Single spores were isolated by spreading 150 ml of spore culture onto micromanipulator plates containing 1×Vogel's salts, 25 mM $NaNO_3$, 2.5% sucrose, 2% Noble agar and 5 mg/ml BASTA and using a micromanipulator to transfer single spores to a clear region of the plate. After 3 days growth at room temperature, the germinated spores were transferred to individual Vogel plates containing 5 mg/ml BASTA.

Culture supernatants from fourteen of the seventeen primary transformants of pMWR48 were positive when assayed for phytase activity. Two primary transformants designated transformant #3 and #5 were selected for single spore isolation based on phytase activity. Nine single spore isolates were obtained. Shake flasks containing 25 ml of M400Da medium plus 5 mg/ml BASTA were inoculated in duplicate with mycelial chunks from each single spore isolate and incubated at 30° C. One ml aliquots of the culture media were harvested at four, five, and seven days post-inoculation and assayed for phytase activity. The results of the phytase assays demonstrated that both primary transformants produced activity.

Example 10
Production of Recombinant *Thermomyces lanuginosus* CBS 586.94 Phytase The primary Fusarium transformant #5 described in Example 9 was cultivated in two 2 liter fermentors for 7 days at 30° C. in a medium at pH 6.25 comprised of 20 g of soy, 20 g of glucose, 10 g of yeast extract, 2 g of $MgSO_4$-$7H_2O$, 2 g of $KH_2PO_4$, 2 g of citric acid, 3 g of $K_2SO_4$, 2 g of $CaCl_2$-$2H_2O$, and 0.5 ml of trace metals solution per liter and fed with a medium comprised of 300 g of glucose, 20 g of $(NH_4)_2HPO_4$, and 1 g of citric acid per liter. A 2.5% inoculum was used for the fermentations. The inoculum was a 48–72 hours shake flask culture comprised of 62.5 g of Nutriose, 2 g of $MgSO_{4-7}H_2O$, 10 g of $KH_2PO_4$, 2 g of $K_2SO_4$, 2 g of citric acid, 10 g of yeast extract, 2 g of urea, 0.5 g of $CaCl_2$, and 0.5 ml of trace metals solution pH 6.0 per liter.

The whole culture broth was filtered using a double layer of MIRACLOTH™ affixed to the top of a 4 liter beaker with rubber bands. The filtrate was recovered and then frozen at 20° C.

Example 11
Purification of Recombinant *Thermomyces lanuginosus* CBS 586.94 Phytase The frozen cell-free broth (1700 ml) described in Example 9 was thawed, clarified by centrifugation at 10,000×g, and concentrated to a volume of 350 ml with an Amicon hollow fiber filtration unit equipped with an Amicon S1Y10 filter (Amicon, Beverly, Mass.). The sample was adjusted to pH 7, diluted to a conductivity of 2 mS, and loaded at room temperature onto a 75 ml bed volume Pharmacia Q-Sepharose Big Beads column (Pharmacia Biotech, Uppsala, Sweden) pre-equilibrated with 20 mM Tris-Cl pH 7 buffer. The column was eluted at a flow rate of 5 ml per minute using the equilibration buffer until the effluent $A_280$ had decreased to near baseline. The column was then eluted with a 600 ml gradient of 0–0.6 M NaCl in the same buffer at a flow rate of 5 ml per minute. Phytase enzyme activity was determined by measuring the hydrolysis rate of 10 mM p-nitrophenyl phosphate in 0.2 M sodium citrate pH 5.5 buffer at 405 nm and 30° C. in a 200 µl reaction volume using a Molecular Devices Thermomax Microplate Reader. The bound enzyme activity eluted in fractions corresponding to ca. 0.2 M NaCl.

The active fractions were pooled and concentrated by ultrafiltration with an Amicon PM-10 membrane (Amicon, Beverly, Mass.) to a volume of 25 ml, diluted to a conductivity of 0.9 mS, and loaded at 4 ml per minute onto a Pharmacia MonoQ HR 10/16 column (Pharmacia Biotech, Uppsala, Sweden) pre-equilibrated in 20 mM MOPS pH 7 buffer. The column was eluted with 80 ml of the equilibration buffer and then with a 400 ml gradient of 0–0.5 M NaCl in the same buffer. Enzyme activity was detected in fractions using the p-nitrophenyl phosphate assay described above. The active fractions were also analyzed with a Novex 10–27% gradient SDS-polyacryamide gel according to the manufacturer's instructions (Novex, San Diego, Calif.) and the fractions were pooled if judged by electrophoresis to be substantially purified.

The pooled fractions were concentrated with an Amicon PM-10 membrane by ultrafiltration and exchanged into 20 mM MES pH 5.5 buffer. The sample conductivity was 1.1 mS. One third of this sample was loaded at 1 ml per minute onto a Pharmacia Mono S HR 5/5 column (Pharmacia Biotech, Uppsala, Sweden) pre-equilibrated with 20 mM MES pH 5.5 buffer. The column was eluted with 5 ml of the equilibration buffer and then with a 25 ml linear gradient of 0–0.6 M sodium chloride in the same buffer. The active fractions were pooled after electrophoretic analysis to eliminate those which contained trace contaminants.

The purified recombinant *Thermomyces lanuginosus* CBS 586.94 phytase appeared homogeneous by SDS-polyacrylamide gel electrophoresis analysis with a single component that had a molecular weight of about 60,000 daltons.

Example 12
Physicochemical Characterization of the Purified Recombinant *Thermomyces lanuginosus* CBS 586.94 Phytase All characterizations were performed with the purified recombinant *Thermomyces lanuginosus* CBS 586.94 phytase described in Example 11. Comparisons were also made where noted with a standard of an *Aspergillus niger* (*ficuum*) phytase obtained from Novo Nordisk AIS, Bagsverd, Denmark.

Isoelectric Point. The isoelectric point (pI) of the Thermomyces phytase was determined to the *Aspergillus niger* phytase. Isoelectric focusing (IEF) was performed with a Novex pH 3–7 IEF gel (Novex, San Diego, Calif.) according to the manufacturer's instructions. IEF standards from both Pharmacia (Pharmacia, Uppsala, Sweden) and BioRad (BioRad Laboratories, Hercules, Calif.) were used to calibrate the gel.

IEF demonstrated that the Thermomyces phytase contained multiple components with pIs in the range of 4.7 to 5.2, whereas the *Aspergillus niger* phytase was observed to possess a pI of 4.8–5.0.

Amino terminal sequence analysis. The purified recombinant Thermomyces phytase was subjected to amino terminal protein sequence analysis on an Applied Biosystems Model 476A Sequencer (Applied Biosystems, Inc., Foster City, Calif.) according to the manufacturer's instructions with liquid phase TFA delivery and on-line HPLC for PTH-amino acid seqparation. Samples were spotted onto a Biobrene™ coated TFA glass fiber filter (Applied Biosystems, Inc., Foster City, Calif.) and sequenced directly.

Amino terminal sequence analysis of the purified phytase revealed three components. The major component (ca. 60%) is $H_2N$-His-Pro-Asn-Val-Asp-Ile-Ala-Arg-His-Trp-Gly-Gln-Tyr-Ser-Pro-Phe-Phe-Ser-Leu-Ala (SEQ ID NO:2) which corresponded to a kex2 cleavage site at position 34 in the primary translation product. Two minor sequences, (ca. 30%) $H_2N$-Gly-Glu-Asp-Glu-Pro-Phe-Val-Arg-Val-Leu-Val-Asn-Asp-Arg-Val-Val-Pro-Leu-His-Gly (SEQ ID NO:2) and (ca. 10%) $H_2N$-Ser-Glu-Glu-Glu-Glu-Glu-Gly-Glu-Asp-Glu-Pro-Phe-Val-Arg-Val-Leu-Val-Asn-Asp-Arg (SEQ ID NO:2) corresponded to internal cleavage sites near the COOH terminal of the protein at positions 428 and 435 in the primary translation product.

Enzyme kinetics studies. Enzyme kinetics studies were performed on the Thermomyces phytase and the *Aspergillus niger* phytase. The studies were accomplished by assay of inorganic phosphate liberated from corn phytic acid (Sigma Chemical Co., St. Louis, Mo.). Standard enzyme reactions were carried out for 30 minutes at 37° C. and pH 5.5 in 0.5% w/w phytic acid. The reaction was quenched by the addition of an equal volume of 15% w/w trichloroacetic acid. After cooling, 100 µl of the resulting mixture was diluted into 1.0 ml of glass distilled water. The sample was incubated at 50° C. for 5 minutes. Color reagent (1.0 ml) was added and the 50° C. incubation was continued for 15 minutes. The absorbance of a 200 µl aliquot was measured at 690 nm with a Molecular Devices Thermomax Microplate Reader. The color reagent is composed of 6 N sulfuric acid: water: 2.5% (w/v) ammonium heptamolybdate, tetrahydrate: 10% ascorbate (aqueous) in a ratio of 1:2:1:1 and prepared fresh on a daily basis. Quantitation was based on a standard curve generated with a 10 mM sodium monobasic phosphate standard. One unit (U) is defined as a µmole of inorganic phosphate released per minute at 37° C. and pH 5.5.

Steady-state kinetics measurements were made by substrate titration. Phytate concentrations were 2.16, 1.08, 0.541, 0.216, 0.108, and 0.0758 mM for the purposes of Km determination. Phytate concentrations of 1.08, 0.541, 0.216 and 0.108 mM in the presence or absence of 1 mM sodium monobasic phosphate were used for the purpose of evaluating product inhibition.

Steady-state kinetic measurements demonstrated that the Thermomyces phytase has an apparent $K_m$ of approximately 110 µM with respect to phytate while *Aspergillus niger* phytase has an apparent $K_m$ of 200 µM. There was a weak indication of excess substrate inhibition at the 2.16 mM substrate concentration, perhaps congruent with the literature report of inhibition above 2 mM for Aspergillus phytase (Ullah, 1988, *Preparative Biochemistry* 18: 443–458). Steady-state kinetic measurements with 1 mM phosphate present failed to reveal any type of inhibition with this product. It was estimated that the $K_i$ for phosphate must exceed 3 mM to be undetectable in our experiments. In contrast, Ullah (Ullah, 1988, supra) has reported that phosphate is a competitive inhibitor of *Aspergillus phytase* with a $K_i$ of 1.9 mM.

Thermostability measurement. The thermostablility of the Thermomyces phytase was compared to the *Aspergillus niger* phytase. Samples of the Thermomyces phytase and the *Aspergillus niger* phytase were dissolved at 100 U per ml in 0.2 M sodium citrate pH 5.5 buffer. Aliquots (100 µl) of each enzyme solution were incubated for 20 minutes in a water bath at the following temperatures: 37, 45, 50, 55, 60, 65, 70 and 75° C. After the temperature treatments, the samples were stored at 0° C. until activity assays were performed. Each sample was diluted 1:80 into 0.2 M sodium citrate pH 5.5 buffer containing 0.01% w/w Tween 20 and the standard activity assay described above was performed.

Figure 6:
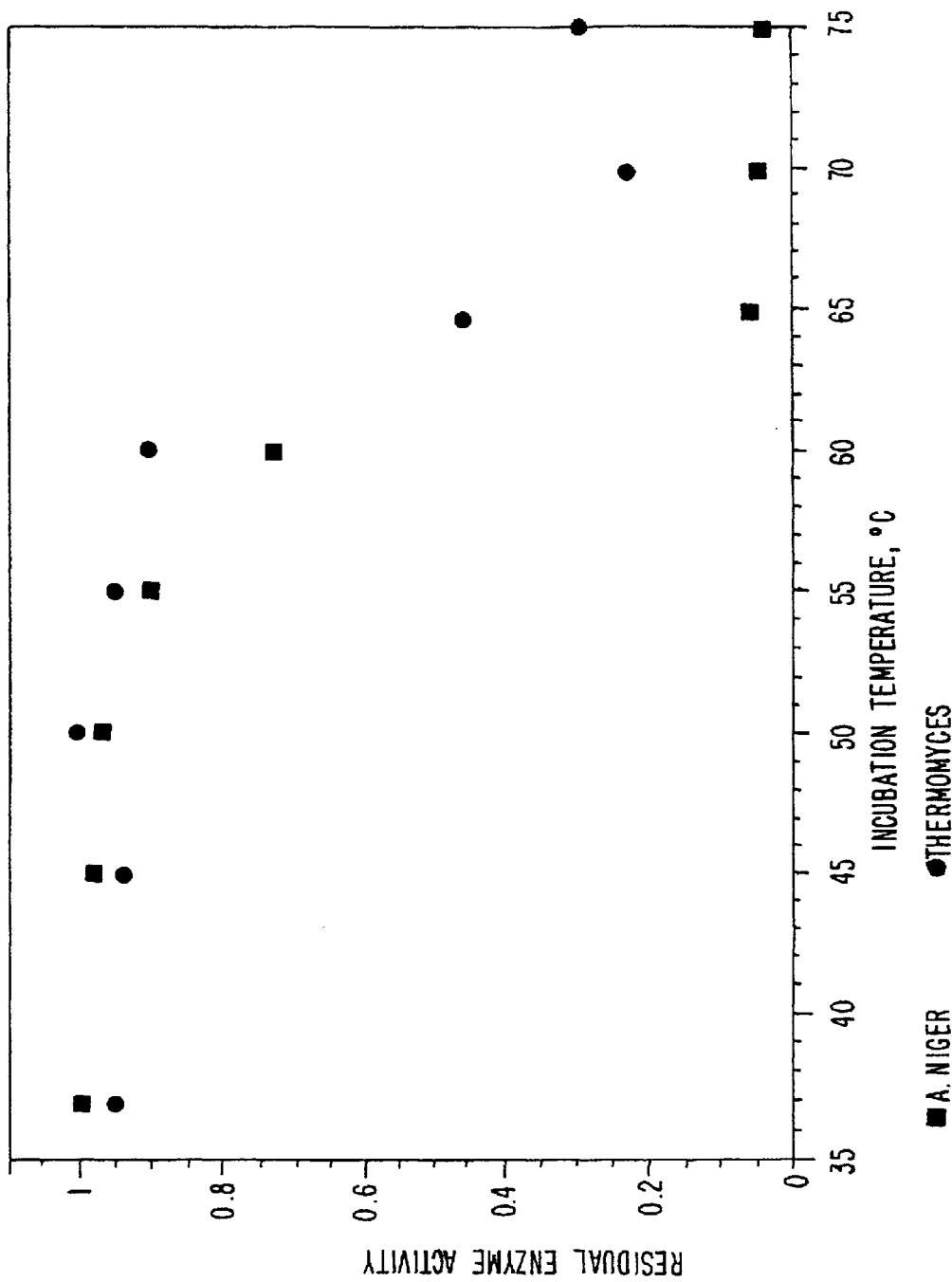
FIG. 6 shows a comparison of the thermostability of the *Thermomyces lanuginosus* CBS 586.94 and *Aspergillus niger* (ficuum). NRRL 3135 phytases.

Comparison of the enzyme thermostability profiles (FIG. 6) suggested that stability differences between the two enzymes are small. However, neither enzyme is fully inactivated by a high temperature incubation and the residual activity profile is consistent with partially reversible thermal denaturation (Ullah and Mullaney, 1996, *Biochem. Biophys. Res. Comm.* 227: 311–317).

pH-activity measurement. The pH-activity profile of the Thermomyces phytase was compared to the *Aspergillus niger* phytase. To attain a buffering range between pH 2–7, a three component 0.125 M glycine-acetate-citrate buffer was employed. The buffer components were combined at final concentrations of 42 mM per component and phytic acid was added as a solid to 1% w/w. This mixture was adjusted to pH 7 with concentrated HCl and a 10 ml aliquot was taken out. This was done for every 0.5 pH increment thereafter through pH 2.

Enzyme stock solutions of 20 U per ml were prepared in 20 mM MES buffer pH 5.5. Substrate (850 microliters) in buffer at a given pH was combined with 100 microliters of water and 50 microliters of enzyme stock solution and incubated for 30 minutes at 37° C. Subsequently the enzyme reaction was quenched with 1 ml of 15% TCA and quantitated by the standard method.

Figure 7:
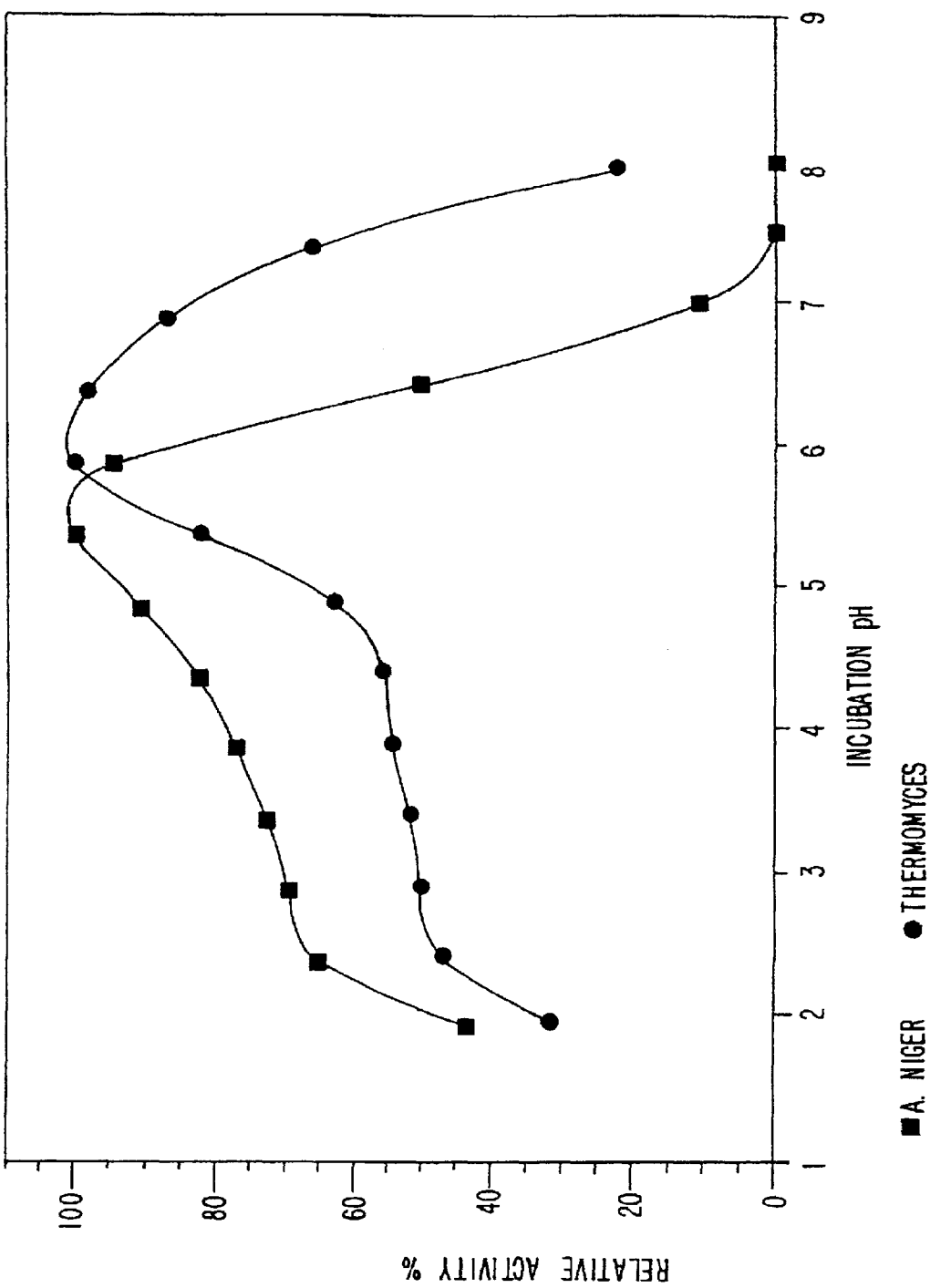
FIG. 7 shows pH-activity profiles of the *Thermomyces lanuginosus* CBS 586.94 and *Aspergillus niger* (ficuum) NRRL 3135 phytases.

The pH-activity profile comparison of Thermomyces and Aspergillus phytase indicated substantial similarity between the two enzymes in pH profile (FIG. 7). However, the Thermozyces phytase is also active at neutral pH while the Aspergillus enzyme is not. Earlier reports in the literature (see, for example, Sandberg, et al., 1996, *J. Nutr.* 126: 476–480) suggest that Aspergillus phytase possesses two pH optima. It is more likely that these reports are based on impure material which contains traces of the Aspergillus acid phosphatase which is well-known in the literature (Zyla, 1993, *World J. Microbiol. Biotechnol.* 9: 117–119).

Temperature-activity measurement. The temperature-activity profile of the Thermomyces phytase was compared to the Aspergillus niger phytase. Enzyme stock solutions of 12.5 U per ml were prepared in 0.2 M sodium citrate pH 5.5 buffer. 250 microliters of 1% phytic acid substrate was added to a 1.7 ml Eppendorf tube followed by 240 microliters of 0.2 M sodium citrate pH 5.5 buffer. This solution was vortexed and placed in a water bath at the designated temperature. After a 20 minute equilibration in the water bath, the Eppendorf tube was vortexed and 10 microliters of phytase solution was added. The sample was vortexed and incubated in the water bath for an additional 30 minutes. After 30 minutes in the water bath, the reaction was quenched with 1 ml of 15% TCA and quantitated by the assay method described above.

Figure 8:
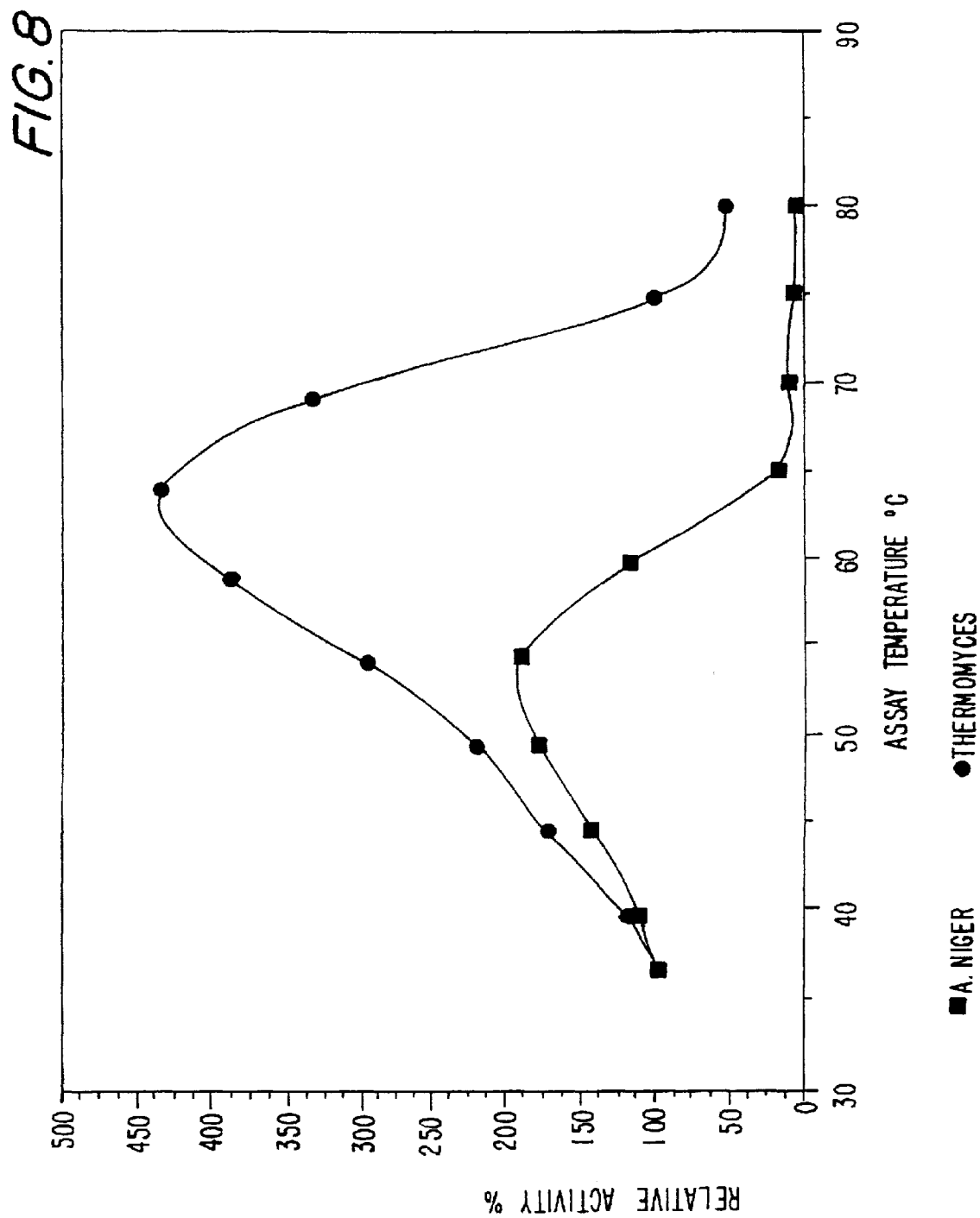
FIG. 8 shows temperature-activity profiles of the *Thermomyces lanuginosus* CBS 586.94 and *Aspergillus niger (ficuum)* NRRL 3135 phytases.

Measurement of enzyme activity as a function of temperature revealed a significant difference between the two enzymes (FIG. 8). Thermomyces phytase displays maximum enzyme activity near 65° C. and has partial activity even at 75° C. while the Aspergillus niger phytase is essentially inactive at 65° C.

Phytate Hydrotysis. A comparison of the ability of Thermomyces and *Aspergillus niger* phytases to hydrolyze phytic acid was made. Each phytase (0.5 U enzyme activity per ml) was incubated with either 0.5% or 0.1% phytic acid at pH 5.5 and 37° C. for 10 hours. The results revealed that *Aspergillus niger* and T7hemonyces phytases released identical amounts (70%) of the total theoretically available phosphorus after 10 hours with either 0.5% or 0.1% phytic acid concentrations.

Example 13
Time-Resolved Product-Profiling of Phytase-Catalyzed Hydrolysis of Phytic Acid by $^1$H NMR Spectroscopy The hydrolysis of phytic acid catalyzed by Thermomyces phytase and by a commercial *Aspergillus niger* phytase (Phytase Novo®) was investigated (27 mM phytate, 1 FYT/ml, pH 5.5, and 27° C.) by $^1$H NMR profiling the product mixture in the course of 24 hours.

In the following (Ins(p,q,r,.)P, denotes myo-inositol carrying in total n phosphate groups attached to positions p, q, r, . . . .

The technique provides specific information about the initial points of attack by the enzyme on phytic acid, as well as information about the identity of the end product. On the other side the evolving patterns of peaks reflecting the composition of the intermediate product mixtures, provide a qualitative measure, a finger print, suitable for identification of similarities and differences between individual enzymes.

NMR spectra were recorded at 300° K. (27° C.) on a Bruker DRX400 instrument equipped with a 5 mm selective inverse probe head. Sixteen scans preceded by 4 dummy scans were accumulated using a sweep width of 2003 Hz (5 ppm) covered by 8 K data points. Attenuation of the residual HOD resonance was achieved by a 3 seconds presaturation period. The spectra were referenced to the HOD signal (b 4.70).

Phytic acid samples for NMR analysis were prepared as follows: phytic acid (100 mg, phytic acid dipotassium salt, Sigma P-5681) was dissolved in deionized water (4.0 ml) and pH adjusted to 5.5 by addition of aqueous NaOH (4 N). Deionized water was added (ad 5 ml) and 1 ml portions, each corresponding to 20 mg of phytic acid, were transferred to screw-cap vials and the solvent evaporated (vacuum centrifuge). The dry samples were dissolved in deuterium oxide (2 ml, Merck 99.5% D) and again evaporated to dryness (stored at −18° C. until use).

For NMR analysis, a 20 mg phytic acid sample was dissolved in deuterium oxide (1.0 ml, Merck 99.95% D). The solution was transferred to an NMR tube and the $^1$H NMR spectrum recorded. Enzyme solution (1 FTU, dissolved in/diluted, as appropriate, with deuterium oxide) was added followed by thorough mixing (1 minute). $^1$H NMR spectra were recorded immediately after adding the enzyme (t=0), then after 5, 10, 15, 20, 25, 30, 45, 60, 75, 90, 105, 120, 135 150, 165, 180, 195, 210 minutes (=3.5 hours), 4.5, 5.5 6.5, 7.5, 8.5, 9.5, 11.5, 13.5, 15.5, 17.5, 19.5, 21.5, and 23.5 hours. The pH in the NMR tube was measured. Additional spectra were acquired after 48 and 120 hours (5 days), where a portion of substrate (6 mg of phytic acid) was added to a probe if the enzyme retained its catalytic activity.

By means of 2D NMR analysis of inositol phosphate mixtures obtained by partial digestion of phytic acid, in conjunction with published NMR data (Scholz, P.; Bergmann, G., and Mayr, G. W. *Methods in Inositide Research* (Ed. Irvine, R. F.), pp. 65–82, Raven Press, Ltd., New York (1990)), characteristic $^1$H NMR signals attributable to Ins(1,2,3,4,5,6)$P_6$ (PA), Ins(1,2,4,5,6)$P_5$, Ins(1,2,3,4,5)$P_5$, Ins(1,2,5,6)P4, Ins(1,2,6)$P_3$, Ins(1,2)$P_2$, and Ins(2)P, were identified and permitted relative quantification of these species during the course of the reaction.

Figure 9:
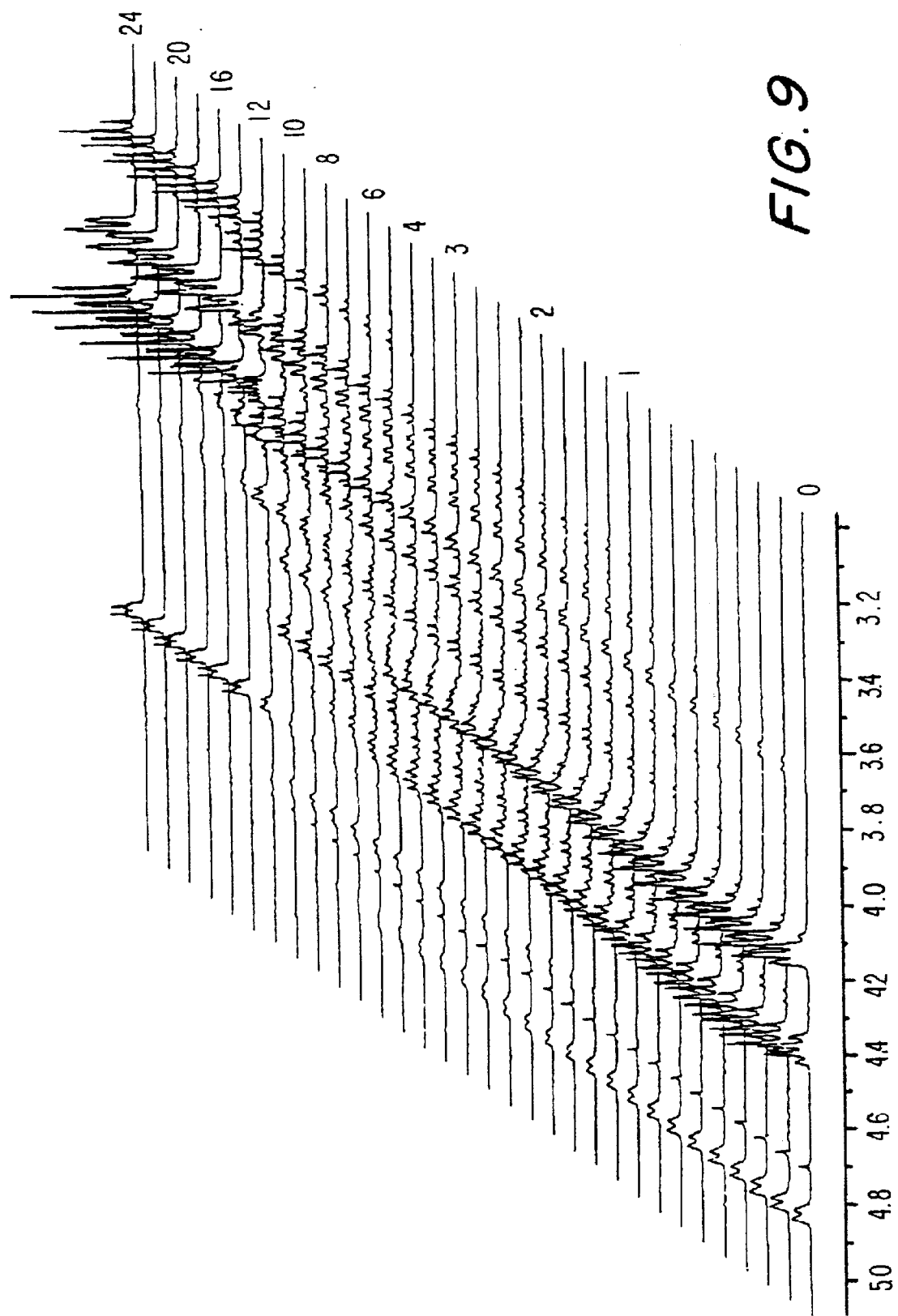
FIG. 9 shows NMR spectra, stacked plots (up to 24 h), showing the product profile of an *Aspergillus niger (ficuum)* phytase.
Figure 10:
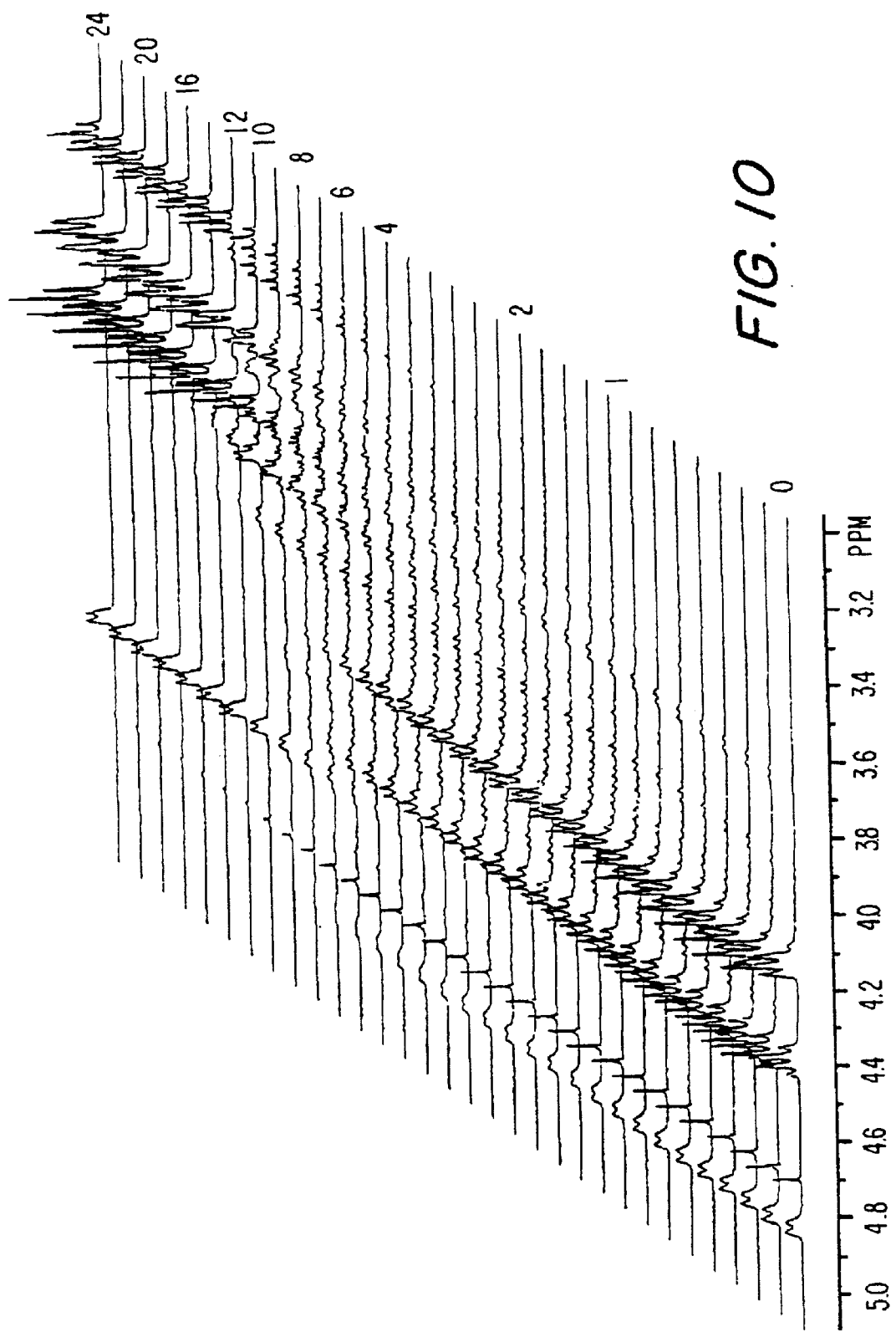
FIG. 10 shows NMR spectra, stacked plots (up to 24 h), showing the product profile of a *Thermomzyces lanuginosus* phytase.

Stacked plots of product profiles for the Aspergillus phytase and the Thermomyces phytase covering 24 hours of reaction time are presented in FIGS. 9 and 10, respectively.

The signal at δ 3.25(t) represents H-5 in Ins(1,2)$P_2$ whereas the signal at δ 3.18(t) represents H-5 in Ins(2)P. Ins(1,2)$P_2$ starts accumulating after about 4 hours of reaction time with the Aspergillus phytase and after about 2 hours of reaction time with the Thermomyces phytase. Ins(2)P is observed after about 10 hours of reaction with the *Aspergillus phytase* and after about 5 hours of reaction with the Thermomyces phytase. After 24 hours of reaction the amount or level of Ins(1,2)$P_2$ is very low for both phytases, whereas the amount of Ins(2)P is maximum for both phytases after 24 hours.

Accordingly, the profiles observed after 24 hours of reaction time demonstrate that both phytases degrade PA to Ins(2)P. The fully dephosphorylated species, inositol (Ins), was not observed at all.

For both enzymes the reaction mixture at 24 h comprised in addition to Ins(2)P minor amounts of Ins(1,2)P2. Prolonged reaction times (several days) resulted in disappearance of the residual Ins(1,2)P$_2$, but the fully dephosphorylated species, inositol (Ins), was not observed at all. The observation is not explained by irreversible inhibition/denaturation of the enzyme, since the enzymes retained their catalytic activities for prolonged periods, as demonstrated by their ability to digest fresh portions of phytic acid added to the NMR tubes after keeping them 5 days at room temperature.

Figure 11:
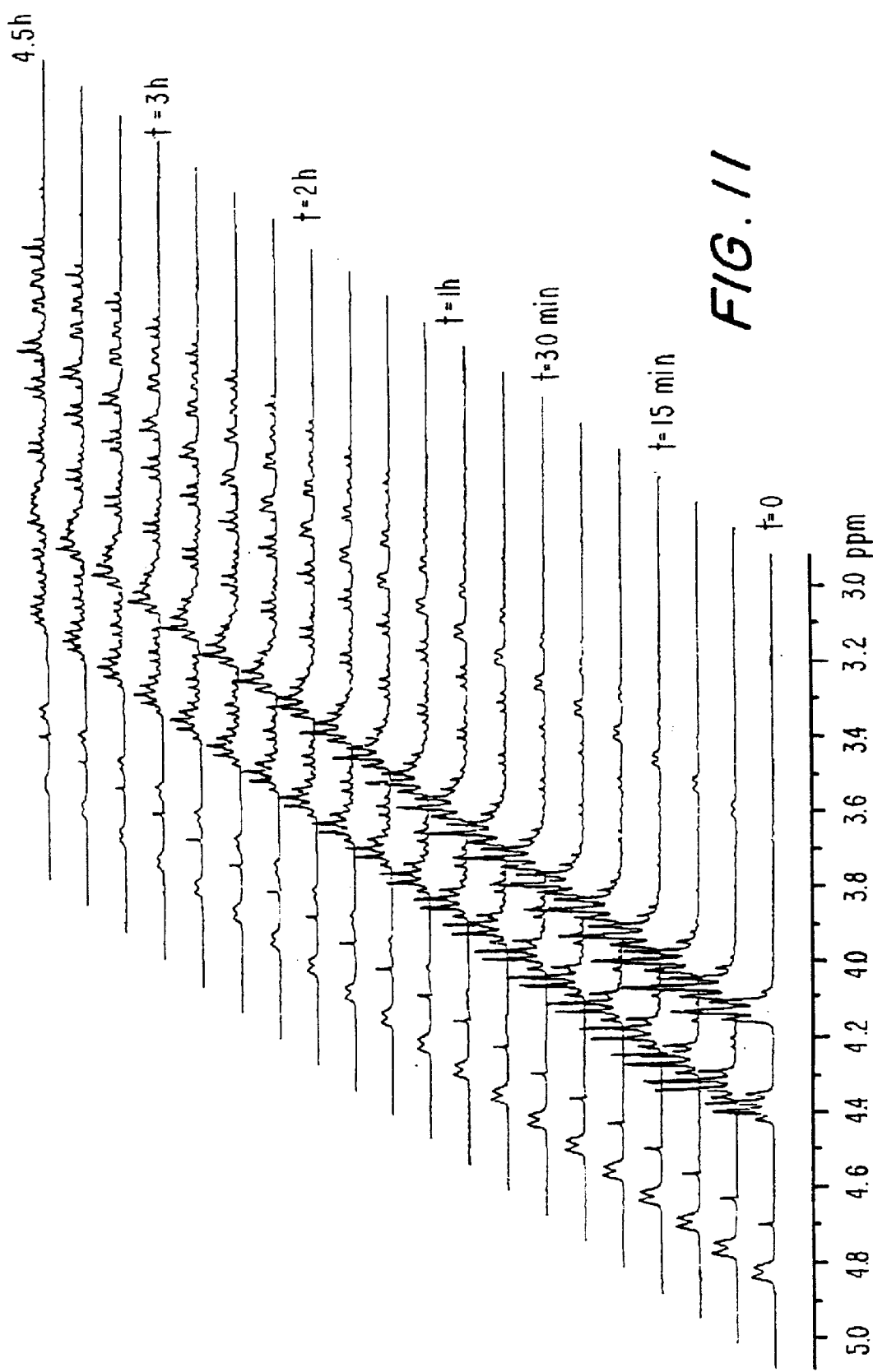
FIG. 11 shows NMR spectra, stacked plots up to 4.5 h, showing the product profile of an *Aspergillus niger (ficuum)* phytase.
Figure 12:
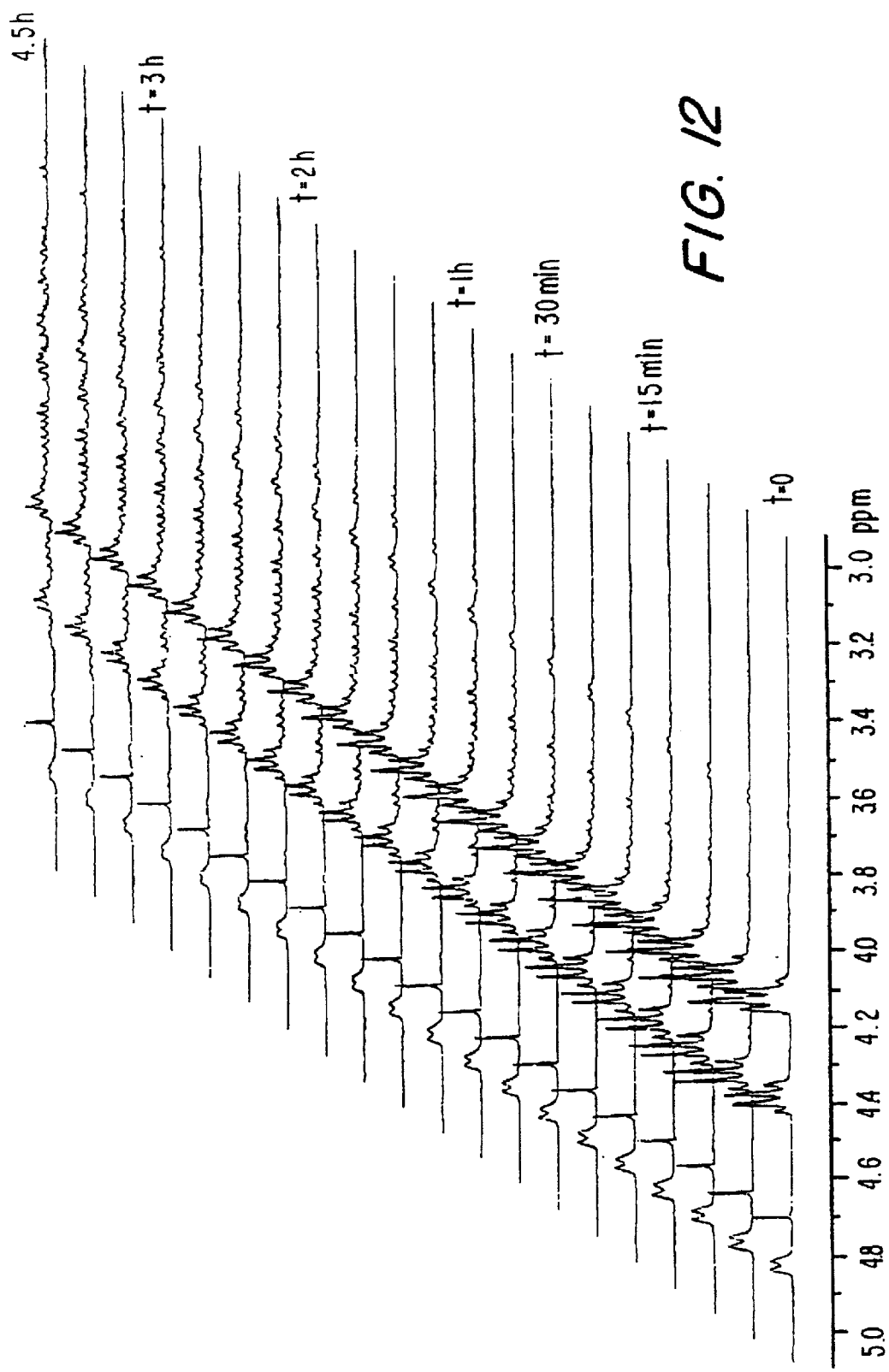
FIG. 12 shows NMR spectra, stacked plots up to 4.5 h, showing the product profile of a *Thermomyces lanuginosus* phytase.

FIGS. 11 and 12 depict in more detail the profiles evolving during the initial 4.5 hours. FIG. 13 shows that H-3 in Ins(1,2,4,5,6)P$_5$ (designated A) shows a signal at δ 3.66(dd), H-6 in Ins(1,2,3,4,5)P$_5$ (B) a signal at δ 3.87(t) and H-3 in Ins(1,2,5,6)P$_4$ (C) a signal at δ 3.56(dd). Compound A corresponds to phosphate in position 3 having been hydrolyzed, B position 6 and C position 3 and 4.

FIG. 11 shows that compound A is the major primary product (t =5 min) using the Aspergillus phytase, whereas compound B does not appear. Compound C appears after 20–25 minutes.

On the other hand, FIG. 12 (the Thermomyces phytase) shows that compound A as well as compound B are produced very early, i.e., within the first 15 minutes, probably more of the compound A than B.

The signals at δ 4.82(dt, H-2), 4.38 (q, H-4/H-6), 4.13(q, H-5) and 4.11(dt,H1/H3) are attributable to the substrate, phytic acid. FIGS. 11 and 12 show that these peaks diminish much faster (i.e., within an hour) with the Thermomyces phytase than with the Aspergillus phytase.

Deposit of Biological Materials

The following strain has been deposited according to the Budapest Treaty in the Agricultural Research Service Patent Culture Collection (NRRL), Northern Regional Research Laboratory, 1815 University Street, Peoria, Ill. 61604, USA. Strain Accession Number Deposit Date E. coli DH5α (pMWR46) NRRL B-21527 Feb. 23, 1996.

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An isolated polypeptide having phytase activity, selected from the group consisting of:
   (a) a polypeptide having an amino acid sequence which has at least 90% identity with amino acids 23 to 475 of SEQ ID NO. 2;
   (b) a polypeptide which is encoded by a nucleic acid sequence which hybridizes under medium stringency conditions with the nucleic acid sequence of SEQ ID NO. 1 or its complementary strand, wherein medium stringency conditions are defined as prehybridization and hybridization at 42° C. in 5×SSPE, 0.3% SDS, 200 μg/ml sheared and denatured salmon sperm DNA, and 35% formamide; and
   (c) a fragment of (a) or (b), wherein the fragment has phytase activity.

2. The polypeptide of claim 1, which is encoded by a nucleic acid sequence which hybridizes under medium stringency conditions with the nucleic acid sequence of SEQ ID NO. 1 or its complementary strand, wherein medium stringency conditions are defined as prehybridization and hybridization at 42° C. in 5×SSPE, 0.3% SDS, 200 μg/ml sheared and denatured salmon sperm DNA, and 35% formamide.

3. The polypeptide of claim 2, which is encoded by a nucleic acid sequence which hybridizes under high stringency conditions with the nucleic acid sequence of SEQ ID NO. 1 or its complementary strand, wherein high stringency conditions are defined as prehybridization and hybridization at 42° C. in 5×SSPE, 0.3% SDS, 200 μg/ml sheared and denatured salmon sperm DNA, and 50% formamide.

4. The polypeptide of claim 1, having an amino acid sequence which has at least 90% identity with amino acids 23 to 475 of SEQ ID NO. 2.

5. The polypeptide of claim 4, having an amino acid sequence which has at least 95% identity with amino acids 23 to 475 of SEQ ID NO. 2.

6. The polypeptide of claim 5, having an amino acid sequence which has at least 97% identity with amino acids 23 to 475 of SEQ ID NO. 2.

7. The polypeptide of claim 1, which has the amino acid sequence of SEQ ID NO. 2 or a fragment thereof which has phytase activity.

8. The polypeptide of claim 7, which has the amino acid sequence of amino acids 23 to 475 of SEQ ID NO. 2.

9. The polypeptide of claim 2, which is obtained from a Thermomyces strain or a synonym or teleomorph thereof.

10. The polypeptide of claim 3, which is obtained from a Thermomyces strain or a synonym or teleomorph thereof.

11. The polypeptide of claim 4, which is obtained from a Thermomyces strain or a synonym or teleomorph thereof.

12. The polypeptide of claim 9, which is obtained from a *Thermomyces lanuginosus* strain or a synonym or teleomorph thereof.

13. The polypeptide of claim 10, which is obtained from a *Thermomyces lanuginosus* strain or a synonym or teleomorph thereof.

14. A food or feed composition comprising a polypeptide of claim 1 and one or more food or feed additives or components.

* * * * *